US012678166B2

(12) United States Patent (10) Patent No.: US 12,678,166 B2
Valdez (45) Date of Patent: Jul. 14, 2026

(54) FLUID BYPASS CONDUIT FOR LEFT ATRIAL PRESSURE MANAGEMENT

(71) Applicant: Edwards Lifesciences Corporation, Irvine, CA (US)

(72) Inventor: Michael G Valdez, Riverside, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 674 days.

(21) Appl. No.: 17/548,443

(22) Filed: Dec. 10, 2021

(65) Prior Publication Data

US 2022/0096087 A1 Mar. 31, 2022

Related U.S. Application Data

(63) Continuation of application No. PCT/US2020/031139, filed on May 1, 2020.

(60) Provisional application No. 62/860,623, filed on Jun. 12, 2019.

(51) Int. Cl.
*A61B 17/11* (2006.01)
*A61B 17/00* (2006.01)
(52) U.S. Cl.
CPC ..... *A61B 17/11* (2013.01); *A61B 2017/00243* (2013.01); *A61B 2017/1107* (2013.01); *A61B 2017/1135* (2013.01)
(58) Field of Classification Search
CPC . A61B 2017/00243; A61B 2017/00252; A61F 2/2487; A61F 2017/00243; A61F 2002/068; A61M 1/3666; A61M 1/36
See application file for complete search history.

(56) References Cited

U.S. PATENT DOCUMENTS 3,538,917 A 11/1970 Selker
3,675,656 A 7/1972 Hakim
3,730,186 A 5/1973 Edmunds et al.
(Continued)

FOREIGN PATENT DOCUMENTS

CN 111317516 A 6/2020
CN 113367839 A 9/2021
(Continued)

OTHER PUBLICATIONS

Bechtold C., et al., "Method for Fabricating Miniaturized NiTi Self-Expandable Thin Film Devices with Increased Radiopacity", Shape Memory and Superelasticity, 2016, vol. 2, pp. 391-398.
(Continued)

*Primary Examiner* — Philip R Wiest
*Assistant Examiner* — Meagan Ngo
(74) *Attorney, Agent, or Firm* — Chang and Hale LLP

(57) ABSTRACT

A method of managing left atrial pressure involves advancing a delivery catheter to a right atrium of a heart of a patient via a transcatheter access path, advancing the delivery catheter through an interatrial septum wall into a left atrium of the heart, deploying a distal end of a bypass fluid conduit from the delivery catheter, anchoring the distal end of the bypass fluid conduit to a pulmonary vein, withdrawing the delivery catheter through the interatrial septum wall, thereby exposing at least a portion of a medial segment of the bypass fluid conduit in the left atrium, anchoring a proximal end of the bypass fluid conduit to the interatrial septum wall, and withdrawing the delivery catheter from the heart.

18 Claims, 11 Drawing Sheets

(56)        References Cited

U.S. PATENT DOCUMENTS

| | | |
|---|---|---|
| 3,853,126 A | 12/1974 | Schulte |
| 3,882,862 A | 5/1975 | Berend |
| 3,882,882 A | 5/1975 | Preisig |
| 3,903,894 A | 9/1975 | Rosen et al. |
| 4,256,094 A | 3/1981 | Kapp et al. |
| 4,428,365 A | 1/1984 | Hakky |
| 4,556,050 A | 12/1985 | Hodgson et al. |
| 4,578,061 A | 3/1986 | Lemelson |
| 4,586,501 A | 5/1986 | Claracq |
| 4,601,718 A | 7/1986 | Possis et al. |
| 4,655,777 A | 4/1987 | Dunn et al. |
| 4,708,140 A | 11/1987 | Baron |
| 4,712,551 A | 12/1987 | Rayhanabad |
| 4,739,762 A | 4/1988 | Palmaz |
| 4,762,128 A | 8/1988 | Rosenbluth |
| 4,774,949 A | 10/1988 | Fogarty |
| 4,828,544 A | 5/1989 | Lane et al. |
| 4,861,336 A | 8/1989 | Helzel |
| 4,881,939 A | 11/1989 | Newman |
| 4,946,457 A | 8/1990 | Elliott |
| 4,950,227 A | 8/1990 | Savin et al. |
| 4,961,729 A | 10/1990 | Vaillancourt |
| 4,997,431 A | 3/1991 | Isner et al. |
| 5,026,377 A | 6/1991 | Burton et al. |
| 5,054,492 A | 10/1991 | Scribner et al. |
| 5,108,420 A | 4/1992 | Marks |
| 5,109,420 A | 4/1992 | Nonaka |
| 5,114,408 A | 5/1992 | Fleischhaker et al. |
| 5,167,239 A | 12/1992 | Cohen et al. |
| 5,190,528 A | 3/1993 | Fonger et al. |
| 5,193,546 A | 3/1993 | Shaknovich |
| 5,201,757 A | 4/1993 | Heyn et al. |
| 5,242,397 A | 9/1993 | Barath et al. |
| 5,242,410 A | 9/1993 | Melker |
| 5,258,042 A | 11/1993 | Mehta |
| 5,267,940 A | 12/1993 | Moulder |
| 5,287,861 A | 2/1994 | Wilk |
| 5,320,613 A | 6/1994 | Houge et al. |
| 5,330,496 A | 7/1994 | Alferness |
| 5,334,217 A | 8/1994 | Das |
| 5,345,940 A | 9/1994 | Seward et al. |
| 5,354,279 A | 10/1994 | Hofling |
| 5,366,490 A | 11/1994 | Edwards et al. |
| 5,373,849 A | 12/1994 | Maroney et al. |
| 5,419,777 A | 5/1995 | Hofling |
| 5,423,878 A | 6/1995 | Franz |
| 5,429,634 A | 7/1995 | Narciso, Jr. |
| 5,431,700 A | 7/1995 | Sloan |
| 5,443,497 A | 8/1995 | Venbrux |
| 5,445,600 A | 8/1995 | Abdulla |
| 5,445,646 A | 8/1995 | Euteneuer et al. |
| 5,456,284 A | 10/1995 | Ryan et al. |
| 5,456,712 A | 10/1995 | Maginot |
| 5,462,523 A | 10/1995 | Samson et al. |
| 5,464,395 A | 11/1995 | Faxon et al. |
| 5,491,224 A | 2/1996 | Bittner et al. |
| 5,492,304 A | 2/1996 | Smith et al. |
| 5,496,311 A | 3/1996 | Abele et al. |
| 5,499,630 A | 3/1996 | Hiki et al. |
| 5,507,724 A | 4/1996 | Hofmann et al. |
| 5,507,725 A | 4/1996 | Savage et al. |
| 5,538,504 A | 7/1996 | Linden et al. |
| 5,551,954 A | 9/1996 | Buscemi et al. |
| 5,554,182 A | 9/1996 | Dinh et al. |
| 5,570,693 A | 11/1996 | Jang et al. |
| 5,571,086 A | 11/1996 | Kaplan et al. |
| 5,571,151 A | 11/1996 | Gregory |
| 5,588,960 A | 12/1996 | Edwards et al. |
| 5,597,146 A | 1/1997 | Putman |
| 5,597,378 A | 1/1997 | Jervis |
| 5,599,300 A | 2/1997 | Weaver et al. |
| 5,614,204 A | 3/1997 | Cochrum |
| 5,628,784 A | 5/1997 | Strecker |
| 5,661,133 A | 8/1997 | Leiden et al. |
| 5,662,609 A | 9/1997 | Slepian |
| 5,662,711 A | 9/1997 | Douglas |
| 5,665,077 A | 9/1997 | Rosen et al. |
| 5,669,880 A | 9/1997 | Solar |
| 5,682,906 A | 11/1997 | Sterman et al. |
| 5,690,670 A | 11/1997 | Davidson |
| 5,693,029 A | 12/1997 | Leonhardt |
| 5,704,361 A | 1/1998 | Seward et al. |
| 5,704,926 A | 1/1998 | Sutton |
| 5,713,363 A | 2/1998 | Seward et al. |
| 5,713,853 A | 2/1998 | Clark et al. |
| 5,718,725 A | 2/1998 | Sterman et al. |
| 5,724,975 A | 3/1998 | Negus et al. |
| 5,724,977 A | 3/1998 | Yock et al. |
| 5,728,123 A | 3/1998 | Lemelson et al. |
| 5,735,847 A | 4/1998 | Gough et al. |
| 5,738,658 A | 4/1998 | Maus et al. |
| 5,743,874 A | 4/1998 | Fischell et al. |
| 5,755,682 A | 5/1998 | Knudson et al. |
| 5,756,696 A | 5/1998 | Gray et al. |
| 5,771,895 A | 6/1998 | Slager |
| 5,772,629 A | 6/1998 | Kaplan |
| 5,772,632 A | 6/1998 | Forman |
| 5,807,258 A | 9/1998 | Cimochowski et al. |
| 5,807,306 A | 9/1998 | Shapland et al. |
| 5,810,780 A | 9/1998 | Brimhall et al. |
| 5,814,005 A | 9/1998 | Barra et al. |
| 5,827,216 A | 10/1998 | Igo et al. |
| 5,830,222 A | 11/1998 | Makower |
| 5,830,224 A | 11/1998 | Cohn et al. |
| 5,836,913 A | 11/1998 | Orth et al. |
| 5,843,090 A | 12/1998 | Schuetz |
| 5,843,170 A | 12/1998 | Ahn |
| 5,944,738 A | 8/1999 | Amplatz et al. |
| 5,951,569 A | 9/1999 | Tuckey et al. |
| 5,954,691 A | 9/1999 | Prosl |
| 5,989,280 A | 11/1999 | Euteneuer et al. |
| 6,019,788 A | 2/2000 | Butters et al. |
| 6,042,589 A | 3/2000 | Marianne |
| 6,053,891 A | 4/2000 | DeCampli |
| 6,081,738 A | 6/2000 | Hinohara et al. |
| 6,086,553 A | 7/2000 | Akbik |
| 6,092,526 A | 7/2000 | Lafontaine et al. |
| 6,095,878 A | 8/2000 | Van Balen |
| 6,113,612 A | 9/2000 | Swanson et al. |
| 6,120,494 A | 9/2000 | Jonkman |
| 6,120,522 A | 9/2000 | Vrba et al. |
| 6,120,534 A | 9/2000 | Ruiz |
| 6,152,937 A | 11/2000 | Peterson et al. |
| 6,165,185 A | 12/2000 | Shennib et al. |
| 6,168,620 B1 | 1/2001 | Kerr |
| 6,168,820 B1 | 1/2001 | Garwood et al. |
| 6,174,681 B1 | 1/2001 | Halling et al. |
| 6,190,353 B1 | 2/2001 | Makower et al. |
| 6,193,734 B1 | 2/2001 | Bolduc et al. |
| 6,196,230 B1 | 3/2001 | Hall et al. |
| 6,241,743 B1 | 6/2001 | Levin et al. |
| 6,248,117 B1 | 6/2001 | Blatter |
| 6,251,116 B1 | 6/2001 | Shennib et al. |
| 6,254,631 B1 | 7/2001 | Thompson |
| 6,280,412 B1 | 8/2001 | Pederson, Jr. et al. |
| 6,283,951 B1 | 9/2001 | Flaherty et al. |
| 6,287,280 B1 | 9/2001 | Lampropoulos et al. |
| 6,287,332 B1 | 9/2001 | Bolz et al. |
| 6,290,728 B1 | 9/2001 | Phelps et al. |
| 6,302,875 B1 | 10/2001 | Makower et al. |
| 6,302,892 B1 | 10/2001 | Wilk |
| 6,302,905 B1 | 10/2001 | Goldsteen et al. |
| 6,309,415 B1 | 10/2001 | Pulnev et al. |
| 6,315,752 B1 | 11/2001 | DiMatteo |
| 6,325,798 B1 | 12/2001 | Edwards et al. |
| 6,361,545 B1 | 3/2002 | MacOviak et al. |
| 6,375,615 B1 | 4/2002 | Flaherty et al. |
| 6,387,116 B1 | 5/2002 | McKenzie et al. |
| 6,387,119 B2 | 5/2002 | Wolf et al. |
| 6,391,036 B1 | 5/2002 | Berg et al. |
| 6,402,767 B1 | 6/2002 | Nash et al. |
| 6,432,127 B1 | 8/2002 | Kim et al. |
| 6,443,158 B1 | 9/2002 | Lafontaine et al. |
| 6,451,048 B1 | 9/2002 | Berg et al. |

(56)  References Cited

U.S. PATENT DOCUMENTS

| | | |
|---|---|---|
| 6,458,140 B2 | 10/2002 | Akin et al. |
| 6,464,665 B1 | 10/2002 | Heuser |
| 6,468,303 B1 | 10/2002 | Amplatz et al. |
| 6,475,226 B1 | 11/2002 | Belef et al. |
| 6,494,889 B1 | 12/2002 | Fleischman et al. |
| 6,503,247 B2 | 1/2003 | Swartz et al. |
| 6,506,201 B2 | 1/2003 | Di Caprio et al. |
| 6,508,824 B1 | 1/2003 | Flaherty et al. |
| 6,561,998 B1 | 5/2003 | Roth et al. |
| 6,562,066 B1 | 5/2003 | Martin |
| 6,575,168 B2 | 6/2003 | Lafontaine et al. |
| 6,579,311 B1 | 6/2003 | Makower |
| 6,589,251 B2 | 7/2003 | Yee et al. |
| 6,595,941 B1 | 7/2003 | Blatter |
| 6,602,241 B2 | 8/2003 | Makower et al. |
| 6,613,074 B1 | 9/2003 | Mitelberg et al. |
| 6,616,624 B1 | 9/2003 | Kieval |
| 6,616,675 B1 | 9/2003 | Evard et al. |
| 6,620,202 B2 | 9/2003 | Bottcher et al. |
| 6,623,494 B1 | 9/2003 | Blatter |
| 6,626,920 B2 | 9/2003 | Whayne |
| 6,638,293 B1 | 10/2003 | Makower et al. |
| 6,692,482 B2 | 2/2004 | Heller et al. |
| 6,695,878 B2 | 2/2004 | McGuckin, Jr. et al. |
| 6,699,256 B1 | 3/2004 | Logan et al. |
| 6,702,828 B2 | 3/2004 | Whayne |
| 6,709,414 B2 | 3/2004 | Weitzel et al. |
| 6,709,444 B1 | 3/2004 | Makower |
| 6,712,836 B1 | 3/2004 | Berg et al. |
| 6,719,804 B2 | 4/2004 | St. Pierre |
| 6,726,659 B1 | 4/2004 | Stocking et al. |
| 6,726,677 B1 | 4/2004 | Flaherty et al. |
| 6,736,825 B2 | 5/2004 | Blatter et al. |
| 6,740,426 B2 | 5/2004 | Kawachi et al. |
| 6,743,244 B2 | 6/2004 | Blatter et al. |
| 6,743,259 B2 | 6/2004 | Ginn |
| 6,746,426 B1 | 6/2004 | Flaherty et al. |
| 6,748,484 B1 | 6/2004 | Henderson et al. |
| 6,758,854 B1 | 7/2004 | Butler et al. |
| 6,776,785 B1 | 8/2004 | Yencho et al. |
| 6,797,083 B2 | 9/2004 | Peterson |
| 6,802,858 B2 | 10/2004 | Gambale et al. |
| 6,805,706 B2 | 10/2004 | Solovay et al. |
| 6,808,498 B2 | 10/2004 | Laroya et al. |
| 6,827,698 B1 | 12/2004 | Kleinekofort |
| 6,847,348 B2 | 1/2005 | Rojewski |
| 6,854,172 B2 | 2/2005 | Kaese et al. |
| 6,858,035 B2 | 2/2005 | Whayne |
| 6,869,437 B1 | 3/2005 | Hausen et al. |
| 6,893,413 B2 | 5/2005 | Martin |
| 6,913,600 B2 | 7/2005 | Valley et al. |
| 6,913,607 B2 | 7/2005 | Ainsworth et al. |
| 6,915,154 B1 | 7/2005 | Docherty et al. |
| 6,926,690 B2 | 8/2005 | Renati |
| 6,972,023 B2 | 12/2005 | Whayne et al. |
| 6,979,351 B2 | 12/2005 | Forsell et al. |
| 6,985,774 B2 | 1/2006 | Kieval et al. |
| 7,002,491 B2 | 2/2006 | Robbins |
| 7,008,397 B2 | 3/2006 | Tweden et al. |
| 7,011,094 B2 | 3/2006 | Rapacki et al. |
| 7,011,678 B2 | 3/2006 | Tenerz et al. |
| 7,025,741 B2 | 4/2006 | Cull |
| 7,025,746 B2 | 4/2006 | Tal |
| 7,037,329 B2 | 5/2006 | Martin |
| 7,056,294 B2 | 6/2006 | Khairkhahan et al. |
| 7,056,320 B2 | 6/2006 | Utley et al. |
| 7,056,325 B1 | 6/2006 | Makower et al. |
| 7,077,860 B2 | 7/2006 | Yan et al. |
| 7,083,631 B2 | 8/2006 | Houser et al. |
| 7,108,701 B2 | 9/2006 | Evens et al. |
| 7,115,136 B2 | 10/2006 | Park et al. |
| 7,118,546 B2 | 10/2006 | Blatter |
| 7,128,750 B1 | 10/2006 | Stergiopulos |
| 7,175,644 B2 | 2/2007 | Cooper et al. |
| 7,182,771 B1 | 2/2007 | Houser et al. |
| 7,235,095 B2 | 6/2007 | Haverkost et al. |
| 7,294,115 B1 | 11/2007 | Wilk |
| 7,316,706 B2 | 1/2008 | Bloom et al. |
| 7,317,951 B2 | 1/2008 | Schneider et al. |
| 7,318,804 B2 | 1/2008 | Weitzel et al. |
| 7,326,221 B2 | 2/2008 | Sakamoto et al. |
| 7,331,985 B2 | 2/2008 | Thompson et al. |
| 7,335,220 B2 | 2/2008 | Khosravi et al. |
| 7,351,247 B2 | 4/2008 | Kupiecki et al. |
| 7,361,181 B2 | 4/2008 | Hindrichs et al. |
| 7,374,567 B2 | 5/2008 | Heuser |
| D581,054 S | 11/2008 | Moore |
| 7,462,162 B2 | 12/2008 | Phan et al. |
| 7,476,200 B2 | 1/2009 | Tal |
| 7,530,963 B2 | 5/2009 | Albright |
| 7,563,277 B2 | 7/2009 | Case et al. |
| 7,623,926 B2 | 11/2009 | Rossing et al. |
| 7,625,593 B2 | 12/2009 | Mandrusov et al. |
| 7,628,768 B2 | 12/2009 | Faul et al. |
| D612,499 S | 3/2010 | Ondracek et al. |
| 7,699,863 B2 | 4/2010 | Marco et al. |
| 7,722,549 B2 | 5/2010 | Nakao |
| 7,722,665 B2 | 5/2010 | Anwar et al. |
| 7,744,621 B2 | 6/2010 | Paul et al. |
| 7,794,495 B2 | 9/2010 | Gale et al. |
| 7,807,191 B2 | 10/2010 | Iyer et al. |
| 7,815,590 B2 | 10/2010 | Cooper |
| 7,815,656 B2 | 10/2010 | Rust et al. |
| 7,815,852 B2 | 10/2010 | Sternby |
| 7,828,814 B2 | 11/2010 | Brenneman et al. |
| 7,846,179 B2 | 12/2010 | Belef et al. |
| 7,846,194 B2 | 12/2010 | Hartley et al. |
| 7,850,705 B2 | 12/2010 | Bachinski et al. |
| 7,867,547 B2 | 1/2011 | Tochterman et al. |
| 7,879,367 B2 | 2/2011 | Heublein et al. |
| 7,892,246 B2 | 2/2011 | Akin et al. |
| 7,892,247 B2 | 2/2011 | Conston et al. |
| 7,923,022 B2 | 4/2011 | Wang et al. |
| 7,951,194 B2 | 5/2011 | Gueriguian et al. |
| 7,959,603 B2 | 6/2011 | Wahr et al. |
| 7,964,210 B2 | 6/2011 | Wang et al. |
| 7,967,769 B2 | 6/2011 | Faul et al. |
| 7,972,346 B2 | 7/2011 | Bachmann et al. |
| 8,002,821 B2 | 8/2011 | Stinson |
| 8,016,782 B2 | 9/2011 | Brenneman et al. |
| 8,048,150 B2 | 11/2011 | Weber et al. |
| 8,052,751 B2 | 11/2011 | Aklog et al. |
| 8,057,534 B2 | 11/2011 | Boismier et al. |
| 8,070,708 B2 | 12/2011 | Rottenberg et al. |
| 8,088,171 B2 | 1/2012 | Brenneman |
| 8,089,029 B2 | 1/2012 | Flanagan |
| 8,091,556 B2 | 1/2012 | Keren et al. |
| 8,128,689 B2 | 3/2012 | Weber et al. |
| 8,182,527 B2 | 5/2012 | Llanos et al. |
| 8,214,015 B2 | 7/2012 | Macaulay et al. |
| 8,221,495 B2 | 7/2012 | Shrivastava et al. |
| 8,226,592 B2 | 7/2012 | Brenneman et al. |
| D665,500 S | 8/2012 | Martin et al. |
| 8,282,591 B2 | 10/2012 | Khan et al. |
| 8,308,682 B2 | 11/2012 | Kramer et al. |
| 8,357,193 B2 | 1/2013 | Phan et al. |
| 8,376,979 B2 | 2/2013 | Kapadia |
| 8,382,697 B2 | 2/2013 | Brenneman et al. |
| D679,015 S | 3/2013 | Nakaji |
| 8,409,167 B2 | 4/2013 | Roschak |
| 8,506,984 B2 | 8/2013 | Cook et al. |
| 8,518,062 B2 | 8/2013 | Cole et al. |
| 8,518,662 B2 | 8/2013 | Ritzen et al. |
| 8,545,552 B2 | 10/2013 | Garrison et al. |
| 8,641,724 B2 | 2/2014 | Brenneman et al. |
| 8,657,790 B2 | 2/2014 | Tal et al. |
| D705,427 S | 5/2014 | Jagger et al. |
| 8,768,487 B2 | 7/2014 | Farnan et al. |
| 8,784,860 B2 | 7/2014 | Falotico et al. |
| 8,882,830 B2 | 11/2014 | Cartledge et al. |
| 8,920,449 B2 | 12/2014 | Wilkinson |
| 8,926,545 B2 | 1/2015 | Brenneman et al. |
| 8,932,341 B2 | 1/2015 | Brenneman |
| D723,166 S | 2/2015 | Igaki et al. |

(56) References Cited

U.S. PATENT DOCUMENTS

| 8,951,276 B2 | 2/2015 | Kellerman et al. |
| 9,044,588 B2 | 6/2015 | Conn |
| 9,056,171 B2 | 6/2015 | Ward et al. |
| 9,061,115 B2 | 6/2015 | Ward et al. |
| 9,067,050 B2 | 6/2015 | Gallagher et al. |
| 9,089,414 B2 | 7/2015 | Zimmerman et al. |
| 9,108,018 B2 | 8/2015 | Dickinson et al. |
| 9,198,756 B2 | 12/2015 | Aklog et al. |
| 9,232,997 B2 | 1/2016 | Sugimoto et al. |
| 9,277,995 B2 | 3/2016 | Celermajer et al. |
| 9,345,485 B2 | 5/2016 | Dakin et al. |
| 9,439,746 B2 | 9/2016 | Bell et al. |
| 9,456,812 B2 | 10/2016 | Finch et al. |
| 9,550,022 B2 | 1/2017 | Brenneman et al. |
| 9,649,480 B2 | 5/2017 | Sugimoto et al. |
| 9,681,948 B2 | 6/2017 | Levi et al. |
| 9,693,800 B2 | 7/2017 | Aman et al. |
| 9,775,636 B2 | 10/2017 | Fazio et al. |
| 9,814,483 B2 | 11/2017 | Vardi |
| 9,827,404 B2 | 11/2017 | Nance et al. |
| 9,872,981 B2 | 1/2018 | Sparks et al. |
| 9,980,815 B2 | 5/2018 | Nitzan et al. |
| 10,292,690 B2 | 5/2019 | Celermajer et al. |
| 10,327,746 B2 | 6/2019 | Glimsdale et al. |
| 10,426,482 B2 | 10/2019 | Rafiee et al. |
| 10,426,497 B2 | 10/2019 | Chou et al. |
| 10,433,851 B2 | 10/2019 | Adams et al. |
| 10,543,113 B2 | 1/2020 | Vong et al. |
| 10,561,423 B2 | 2/2020 | Sharma |
| 10,565,835 B2 | 2/2020 | Harrington et al. |
| 10,568,751 B2 | 2/2020 | McNamara |
| 10,595,999 B2 | 3/2020 | Vettukattil et al. |
| 10,709,451 B2 | 7/2020 | Gronberg et al. |
| 10,835,394 B2 | 11/2020 | Nae et al. |
| 10,898,698 B1 | 1/2021 | Eigler et al. |
| 10,912,585 B2 | 2/2021 | Kleyman |
| 10,925,756 B2 | 2/2021 | Perszyk |
| 10,940,296 B2 | 3/2021 | Keren |
| 11,135,054 B2 | 10/2021 | Nitzan et al. |
| 11,234,702 B1 | 2/2022 | Eigler et al. |
| 11,291,807 B2 | 4/2022 | Eigler et al. |
| 11,298,117 B2 | 4/2022 | Hariton et al. |
| 11,304,698 B2 | 4/2022 | Sharma |
| 2001/0000041 A1 | 3/2001 | Selmon et al. |
| 2001/0025643 A1 | 10/2001 | Foley |
| 2001/0035183 A1 | 11/2001 | Sexton et al. |
| 2001/0045698 A1 | 11/2001 | Lo |
| 2001/0047165 A1 | 11/2001 | Makower et al. |
| 2002/0013616 A1 | 1/2002 | Carter et al. |
| 2002/0029079 A1 | 3/2002 | Kim et al. |
| 2002/0062146 A1 | 5/2002 | Makower et al. |
| 2002/0128546 A1 | 9/2002 | Silver |
| 2002/0138009 A1 | 9/2002 | Brockway et al. |
| 2002/0169466 A1 | 11/2002 | Peterson et al. |
| 2002/0193751 A1 | 12/2002 | Theeuwes et al. |
| 2002/0198501 A1 | 12/2002 | Kumar et al. |
| 2003/0017150 A1 | 1/2003 | Torphy |
| 2003/0060876 A1 | 3/2003 | Loshakove et al. |
| 2003/0065345 A1 | 4/2003 | Weadock |
| 2003/0181928 A1 | 9/2003 | Vidlund et al. |
| 2003/0225425 A1 | 12/2003 | Kupiecki et al. |
| 2004/0064081 A1 | 4/2004 | Stanish |
| 2004/0082738 A1 | 4/2004 | Dolle et al. |
| 2004/0087997 A1 | 5/2004 | Brenneman |
| 2004/0092879 A1 | 5/2004 | Kraus et al. |
| 2004/0098105 A1 | 5/2004 | Stinson et al. |
| 2004/0158143 A1 | 8/2004 | Flaherty et al. |
| 2004/0215168 A1 | 10/2004 | Verrier et al. |
| 2004/0215220 A1 | 10/2004 | Dolan et al. |
| 2004/0215323 A1 | 10/2004 | Stiger |
| 2004/0230156 A1 | 11/2004 | Schreck et al. |
| 2004/0260318 A1 | 12/2004 | Hunter et al. |
| 2005/0021085 A1 | 1/2005 | Abrams et al. |
| 2005/0033239 A1 | 2/2005 | Argentine |
| 2005/0038501 A1 | 2/2005 | Moore et al. |
| 2005/0043708 A1 | 2/2005 | Gleeson et al. |
| 2005/0049675 A1 | 3/2005 | Wallace |
| 2005/0060041 A1 | 3/2005 | Phan et al. |
| 2005/0065469 A1 | 3/2005 | Tal |
| 2005/0075655 A1 | 4/2005 | Bumbalough et al. |
| 2005/0075656 A1 | 4/2005 | Beaupre |
| 2005/0082226 A1 | 4/2005 | Bene et al. |
| 2005/0107723 A1 | 5/2005 | Wehman et al. |
| 2005/0149096 A1 | 7/2005 | Hilal et al. |
| 2005/0165344 A1 | 7/2005 | Dobak |
| 2005/0228402 A1 | 10/2005 | Hofmann |
| 2005/0249770 A1 | 11/2005 | Hunter |
| 2005/0249776 A1 | 11/2005 | Chen et al. |
| 2005/0267490 A1 | 12/2005 | Secrest et al. |
| 2005/0272806 A1 | 12/2005 | Falotico et al. |
| 2005/0277965 A1 | 12/2005 | Brenneman et al. |
| 2006/0020324 A1 | 1/2006 | Schmid et al. |
| 2006/0024359 A1 | 2/2006 | Walker et al. |
| 2006/0034466 A1 | 2/2006 | Form et al. |
| 2006/0041270 A1 | 2/2006 | Lenker et al. |
| 2006/0074398 A1 | 4/2006 | Whiting et al. |
| 2006/0111704 A1 | 5/2006 | Brenneman et al. |
| 2006/0130591 A1 | 6/2006 | Perkins |
| 2006/0130767 A1 | 6/2006 | Herchen |
| 2006/0182536 A1 | 8/2006 | Rice et al. |
| 2006/0198869 A1 | 9/2006 | Furst et al. |
| 2006/0241342 A1 | 10/2006 | MacAulay et al. |
| 2006/0264801 A1 | 11/2006 | Bolling et al. |
| 2006/0265042 A1 | 11/2006 | Catanese et al. |
| 2006/0271196 A1 | 11/2006 | Saal et al. |
| 2006/0293701 A1 | 12/2006 | Ainsworth et al. |
| 2007/0010781 A1 | 1/2007 | Vijay |
| 2007/0021730 A1 | 1/2007 | Flaherty et al. |
| 2007/0083258 A1 | 4/2007 | Falotico et al. |
| 2007/0173787 A1 | 7/2007 | Huang et al. |
| 2007/0179426 A1 | 8/2007 | Selden |
| 2007/0213750 A1 | 9/2007 | Weadock |
| 2008/0021485 A1 | 1/2008 | Catanese et al. |
| 2008/0027532 A1 | 1/2008 | Boylan et al. |
| 2008/0051883 A1 | 2/2008 | Llanos et al. |
| 2008/0071178 A1 | 3/2008 | Greenland et al. |
| 2008/0091264 A1 | 4/2008 | MacHold et al. |
| 2008/0109069 A1 | 5/2008 | Coleman et al. |
| 2008/0161904 A1 | 7/2008 | Heuser et al. |
| 2008/0167595 A1 | 7/2008 | Porter et al. |
| 2008/0234842 A1 | 9/2008 | Zhang |
| 2008/0306359 A1 | 12/2008 | Zdeblick et al. |
| 2009/0005656 A1 | 1/2009 | Najafi et al. |
| 2009/0043381 A1 | 2/2009 | Macoviak et al. |
| 2009/0105654 A1 | 4/2009 | Kurth et al. |
| 2009/0125097 A1 | 5/2009 | Bruszewski et al. |
| 2009/0143713 A1 | 6/2009 | Van Dam et al. |
| 2009/0149947 A1 | 6/2009 | Frohwitter |
| 2009/0187116 A1 | 7/2009 | Noishiki et al. |
| 2009/0234293 A1 | 9/2009 | Albrecht et al. |
| 2009/0281379 A1 | 11/2009 | Binmoeller et al. |
| 2010/0016797 A1 | 1/2010 | Rockrohr |
| 2010/0022940 A1 | 1/2010 | Thompson |
| 2010/0030321 A1 | 2/2010 | Mach |
| 2010/0106171 A1 | 4/2010 | Arepally et al. |
| 2010/0198041 A1 | 8/2010 | Christian et al. |
| 2010/0217382 A1 | 8/2010 | Chau et al. |
| 2010/0298930 A1 | 11/2010 | Orlov |
| 2011/0096036 A1 | 4/2011 | McIntosh et al. |
| 2011/0106118 A1 | 5/2011 | Son et al. |
| 2011/0251482 A1 | 10/2011 | Kellerman et al. |
| 2011/0306916 A1 | 12/2011 | Nitzan et al. |
| 2012/0022427 A1* | 1/2012 | Kapadia ............ A61B 17/0057 |
| | | 604/8 |
| 2012/0029598 A1 | 2/2012 | Zhao |
| 2012/0041544 A1 | 2/2012 | Wolf |
| 2012/0053686 A1 | 3/2012 | McNamara et al. |
| 2012/0108986 A1 | 5/2012 | Beasley et al. |
| 2012/0143141 A1 | 6/2012 | Verkaik et al. |
| 2012/0265229 A1 | 10/2012 | Rottenberg et al. |
| 2012/0265296 A1 | 10/2012 | McNamara et al. |
| 2013/0022214 A1 | 1/2013 | Dickins et al. |
| 2013/0030521 A1 | 1/2013 | Nitzan et al. |
| 2013/0046152 A1 | 2/2013 | Najafi et al. |

(56)      References Cited

U.S. PATENT DOCUMENTS

| | | |
|---|---|---|
| 2013/0178784 A1 | 7/2013 | McNamara et al. |
| 2013/0204175 A1 | 8/2013 | Sugimoto |
| 2013/0225997 A1 | 8/2013 | Dillard et al. |
| 2013/0253342 A1 | 9/2013 | Griswold et al. |
| 2013/0281988 A1 | 10/2013 | Magnin et al. |
| 2014/0094836 A1 | 4/2014 | Feng et al. |
| 2014/0183828 A1 | 7/2014 | Xu et al. |
| 2014/0203939 A1 | 7/2014 | Harrington et al. |
| 2014/0222040 A1 | 8/2014 | Park et al. |
| 2014/0228733 A1 | 8/2014 | Martinez et al. |
| 2014/0276395 A1 | 9/2014 | Wilson et al. |
| 2014/0277054 A1 | 9/2014 | McNamara et al. |
| 2014/0278442 A1 | 9/2014 | Hong et al. |
| 2014/0288480 A1* | 9/2014 | Zimmerman ........... A61F 2/848 |
| | | 606/108 |
| 2014/0350523 A1 | 11/2014 | Dehdashtian et al. |
| 2015/0119796 A1 | 4/2015 | Finch |
| 2015/0148731 A1 | 5/2015 | McNamara et al. |
| 2015/0151101 A1 | 6/2015 | Bonnette et al. |
| 2015/0238729 A1 | 8/2015 | Jenson et al. |
| 2016/0022293 A1 | 1/2016 | Dubrul et al. |
| 2016/0022970 A1 | 1/2016 | Forcucci et al. |
| 2016/0045165 A1 | 2/2016 | Braido et al. |
| 2016/0058452 A1 | 3/2016 | Brenneman et al. |
| 2016/0089238 A1 | 3/2016 | Centola et al. |
| 2016/0120550 A1 | 5/2016 | Mcnamara et al. |
| 2016/0151615 A1 | 6/2016 | Overtoom |
| 2016/0220357 A1 | 8/2016 | Anand et al. |
| 2016/0228246 A1 | 8/2016 | Zimmerman |
| 2016/0270810 A1 | 9/2016 | Vardi et al. |
| 2016/0296317 A1 | 10/2016 | Timmermans et al. |
| 2016/0323977 A1 | 11/2016 | Sun et al. |
| 2016/0331468 A1 | 11/2016 | Lee et al. |
| 2016/0338823 A1 | 11/2016 | Akingba |
| 2017/0090865 A1 | 3/2017 | Armstrong-Muntner et al. |
| 2017/0105839 A1 | 4/2017 | Subramanian et al. |
| 2017/0106176 A1* | 4/2017 | Taft ..................... A61M 27/008 |
| 2017/0113026 A1 | 4/2017 | Finch |
| 2017/0128705 A1 | 5/2017 | Forcucci et al. |
| 2017/0196565 A1 | 7/2017 | Tuseth et al. |
| 2017/0258585 A1 | 9/2017 | Marquez et al. |
| 2017/0303959 A1 | 10/2017 | Feng et al. |
| 2017/0319823 A1 | 11/2017 | Yacoby et al. |
| 2017/0340460 A1 | 11/2017 | Rosen et al. |
| 2018/0035971 A1 | 2/2018 | Brenner et al. |
| 2018/0140444 A1 | 5/2018 | Neuss et al. |
| 2018/0177516 A1 | 6/2018 | Vardi et al. |
| 2018/0185153 A1 | 7/2018 | Bishop et al. |
| 2018/0207412 A1 | 7/2018 | Malek et al. |
| 2018/0214269 A1 | 8/2018 | Wilson et al. |
| 2018/0243071 A1 | 8/2018 | Eigler et al. |
| 2018/0256865 A1 | 9/2018 | Finch et al. |
| 2018/0303488 A1* | 10/2018 | Hill .................... A61B 18/1492 |
| 2019/0008628 A1 | 1/2019 | Eigler et al. |
| 2019/0046270 A1* | 2/2019 | Belson ............... A61B 18/1492 |
| 2019/0083076 A1* | 3/2019 | Alanbaei ............ A61B 17/0057 |
| 2019/0083228 A1 | 3/2019 | Dickinson et al. |
| 2019/0134350 A1 | 5/2019 | Crisco et al. |
| 2019/0269392 A1 | 9/2019 | Celermajer et al. |
| 2019/0298909 A1 | 10/2019 | Cully et al. |
| 2019/0336339 A1 | 11/2019 | Reo et al. |
| 2019/0351210 A1 | 11/2019 | Solomon et al. |
| 2020/0054867 A1 | 2/2020 | Schwartz et al. |
| 2020/0085600 A1 | 3/2020 | Schwartz et al. |
| 2020/0101270 A1 | 4/2020 | Sutherland |
| 2020/0170662 A1 | 6/2020 | Vardi et al. |
| 2020/0187945 A1 | 6/2020 | Rowe et al. |
| 2020/0230362 A1 | 7/2020 | Basude |
| 2020/0254228 A1 | 8/2020 | Taft et al. |
| 2020/0261704 A1 | 8/2020 | Wang et al. |
| 2020/0289196 A1 | 9/2020 | Arevalos et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0007790 A1 | 1/2021 | Takahashi et al. |

| | | |
|---|---|---|
| 2021/0007791 A1 | 1/2021 | Takahashi et al. |
| 2021/0007800 A1 | 1/2021 | Takahashi et al. |
| 2021/0022855 A1 | 1/2021 | Tegels et al. |
| 2021/0045691 A1 | 2/2021 | Zou et al. |
| 2021/0052877 A1 | 2/2021 | Muldoon et al. |
| 2021/0059650 A1 | 3/2021 | Eidenschink et al. |
| 2021/0077186 A1 | 3/2021 | Pate et al. |
| 2021/0085935 A1 | 3/2021 | Fahey et al. |
| 2021/0092522 A1 | 3/2021 | Draper et al. |
| 2021/0113824 A1 | 4/2021 | Chng et al. |
| 2021/0121179 A1 | 4/2021 | Ben-David et al. |
| 2021/0137635 A1 | 5/2021 | Gomez et al. |
| 2021/0153776 A1 | 5/2021 | Minar et al. |
| 2021/0161637 A1 | 6/2021 | Eigler et al. |
| 2021/0177508 A1 | 6/2021 | Kellerman |
| 2021/0213269 A1 | 7/2021 | Venskytis et al. |
| 2021/0236138 A1 | 8/2021 | Perszyk et al. |
| 2021/0259671 A1 | 8/2021 | DiCicco et al. |
| 2021/0290214 A1 | 9/2021 | Cole et al. |
| 2021/0338990 A1 | 11/2021 | Eigler et al. |
| 2021/0361238 A1 | 11/2021 | Bak-Boychuk et al. |
| 2021/0369321 A1 | 12/2021 | Yang et al. |
| 2021/0401494 A1 | 12/2021 | Passman et al. |
| 2022/0001154 A1 | 1/2022 | Rowe et al. |
| 2022/0008014 A1 | 1/2022 | Rowe et al. |
| 2022/0031327 A1 | 2/2022 | Manash et al. |
| 2022/0039667 A1 | 2/2022 | Schmitt et al. |
| 2022/0039671 A1 | 2/2022 | Fahey |
| 2022/0039833 A1 | 2/2022 | Thai et al. |
| 2022/0088355 A1 | 3/2022 | Rabito et al. |
| 2022/0110679 A1 | 4/2022 | Wang et al. |
| 2022/0142652 A1 | 5/2022 | Alexander et al. |
| 2022/0151784 A1 | 5/2022 | Eigler et al. |
| 2022/0168015 A1 | 6/2022 | Murray et al. |
| 2022/0184356 A1 | 6/2022 | Nae et al. |
| 2022/0202443 A1 | 6/2022 | Thai et al. |
| 2022/0203077 A1 | 6/2022 | Folan |
| 2022/0203078 A1 | 6/2022 | May |
| 2022/0211380 A1 | 7/2022 | Pate |
| 2022/0218352 A1 | 7/2022 | O'Halloran et al. |
| 2022/0218964 A1 | 7/2022 | Fahey et al. |
| 2022/0241564 A1 | 8/2022 | Shang et al. |
| 2022/0241565 A1 | 8/2022 | Nae et al. |
| 2022/0249285 A1 | 8/2022 | Chang et al. |
| 2022/0257904 A1 | 8/2022 | Passman et al. |
| 2022/0273279 A1 | 9/2022 | Valdez et al. |
| 2022/0280160 A1 | 9/2022 | Sharma |
| 2022/0280760 A1 | 9/2022 | Thai et al. |
| 2022/0296865 A1 | 9/2022 | Rafiee et al. |
| 2022/0313234 A1 | 10/2022 | McNamara et al. |
| 2022/0323012 A1 | 10/2022 | Pool et al. |
| 2022/0323196 A1 | 10/2022 | Rafiee et al. |
| 2022/0346936 A1 | 11/2022 | Scutti et al. |
| 2022/0347446 A1 | 11/2022 | Fahey et al. |
| 2022/0370120 A1 | 11/2022 | Yang et al. |
| 2022/0379100 A1 | 12/2022 | Gutierrez et al. |
| 2022/0387009 A1 | 12/2022 | Bukhdruker et al. |
| 2023/0099410 A1 | 3/2023 | Primeaux |
| 2023/0165672 A1 | 6/2023 | Fahey et al. |
| 2023/0181214 A1 | 6/2023 | Vardi et al. |
| 2023/0191093 A1 | 6/2023 | Nae et al. |
| 2023/0233255 A1 | 7/2023 | Takahashi |
| 2023/0263949 A1 | 8/2023 | Passman et al. |
| 2023/0285133 A1 | 9/2023 | Eigler et al. |
| 2023/0330398 A1 | 10/2023 | Nae et al. |
| 2023/0371902 A1 | 11/2023 | Valdez |
| 2023/0389811 A1 | 12/2023 | Valdez |
| 2023/0404659 A1 | 12/2023 | Akerele-Ale et al. |
| 2024/0000404 A1 | 1/2024 | Robertson et al. |

FOREIGN PATENT DOCUMENTS

| | | |
|---|---|---|
| CN | 113397762 A | 9/2021 |
| EP | 3000437 A1 | 3/2016 |
| KR | 20200145957 A | 12/2020 |
| WO | WO-2005006963 A2 | 1/2005 |
| WO | WO-2014150106 A1 | 9/2014 |
| WO | WO-2015052235 A1 | 4/2015 |
| WO | WO-2017217932 A1 | 12/2017 |

(56)　　　　References Cited

FOREIGN PATENT DOCUMENTS

| WO | WO-2019035993 A1 | 2/2019 |
| WO | WO-2019052610 A1 | 3/2019 |
| WO | WO-2020215090 A1 | 10/2020 |
| WO | WO-2020232384 A1 | 11/2020 |
| WO | WO-2021091566 A1 | 5/2021 |
| WO | WO-2022031317 A1 | 2/2022 |
| WO | WO-2022060630 A1 | 3/2022 |
| WO | WO-2022071179 A1 | 4/2022 |
| WO | WO-2022133070 A1 | 6/2022 |
| WO | WO-2022169865 A1 | 8/2022 |
| WO | WO-2022177737 A1 | 8/2022 |
| WO | WO-2022197454 A1 | 9/2022 |
| WO | WO-2022197455 A1 | 9/2022 |
| WO | WO-2022232133 A1 | 11/2022 |
| WO | WO-2022246158 A1 | 11/2022 |
| WO | WO-2022246166 A1 | 11/2022 |
| WO | WO-2022271473 A1 | 12/2022 |
| WO | WO-2023022883 A1 | 2/2023 |
| WO | WO-2023027926 A1 | 3/2023 |
| WO | WO-2023079498 A1 | 5/2023 |
| WO | WO-2023081127 A1 | 5/2023 |
| WO | WO-2023081129 A1 | 5/2023 |
| WO | WO-2023154235 A1 | 8/2023 |
| WO | WO-2023154308 A1 | 8/2023 |
| WO | WO-2023172435 A1 | 9/2023 |
| WO | WO-2023172436 A1 | 9/2023 |
| WO | WO-2023196243 A1 | 10/2023 |
| WO | WO-2023239784 A1 | 12/2023 |
| WO | WO-2023239785 A1 | 12/2023 |
| WO | WO-2023239788 A2 | 12/2023 |
| WO | WO-2024076579 A1 | 4/2024 |

OTHER PUBLICATIONS

Chao-Chi Y., et al., "Fabrication of a Flexible Wireless Pressure Sensor for Intravascular Blood Pressure Monitoring," Microelectronic Engineering Elsevier Publishers Bv, Amsterdam, NL, Apr. 11, 2019, vol. 213, pp. 55-61, ISSN 0167-9317, XP085679189, Retrieved from URL: http://dx.doi.Org/10.1016/j.mee.2019.04.009.

Kong H., et al., "Creation Of An Intra-atrial Communication With A New Amplatzer Shunt Prosthesis: Preliminary Resultsin a Swinw Model," Catheterization and Cardiovascular Interventions, 2002, vol. 56, pp. 267-271.

Kong P.K., et al., "Unroofed Coronary Sinus and Persistent Left Superior Vena Cava," The European Society of Cardiology, 2006, pp. 398-401.

Mantini E., MD, et al., "Congenital Anomalies Involving the Coronary Sinus," Circulation, Journal of the American Heart Association, Feb. 1966, vol. 33, pp. 317-327.

Ruebben A., etal, "Arteriovenous Fistulas Induced by Femoral Arterial Catheterization: Percutaneous Treatment," Radiology, Dec. 1998, vol. 209, No. 3, pp. 729-734.

Scheller V., et al., "Coronary Sinus to Left Atrial Communication," Case Report in Medicine, Ohio Heart and Vascular Center, 2009, vol. 2009, Article ID 790715, 4 Pages.

* cited by examiner

400

ADVANCE DELIVERY CATHETER TO RIGHT ATRIUM PERCUTANEOUSLY/ THROUGH TRANSCATHETER ACCESS PATH

402

ADVANCE DELIVERY CATHETER THROUGH INTERATRIAL SEPTUM INTO LEFT ATRIUM

404

ADVANCE DELIVERY CATHETER INTO OR ADJACENT TO PULMONARY VEIN

406

ANCHOR 1ST END OF BYPASS CONDUIT DEVICE TO PULMONARY VEIN

408

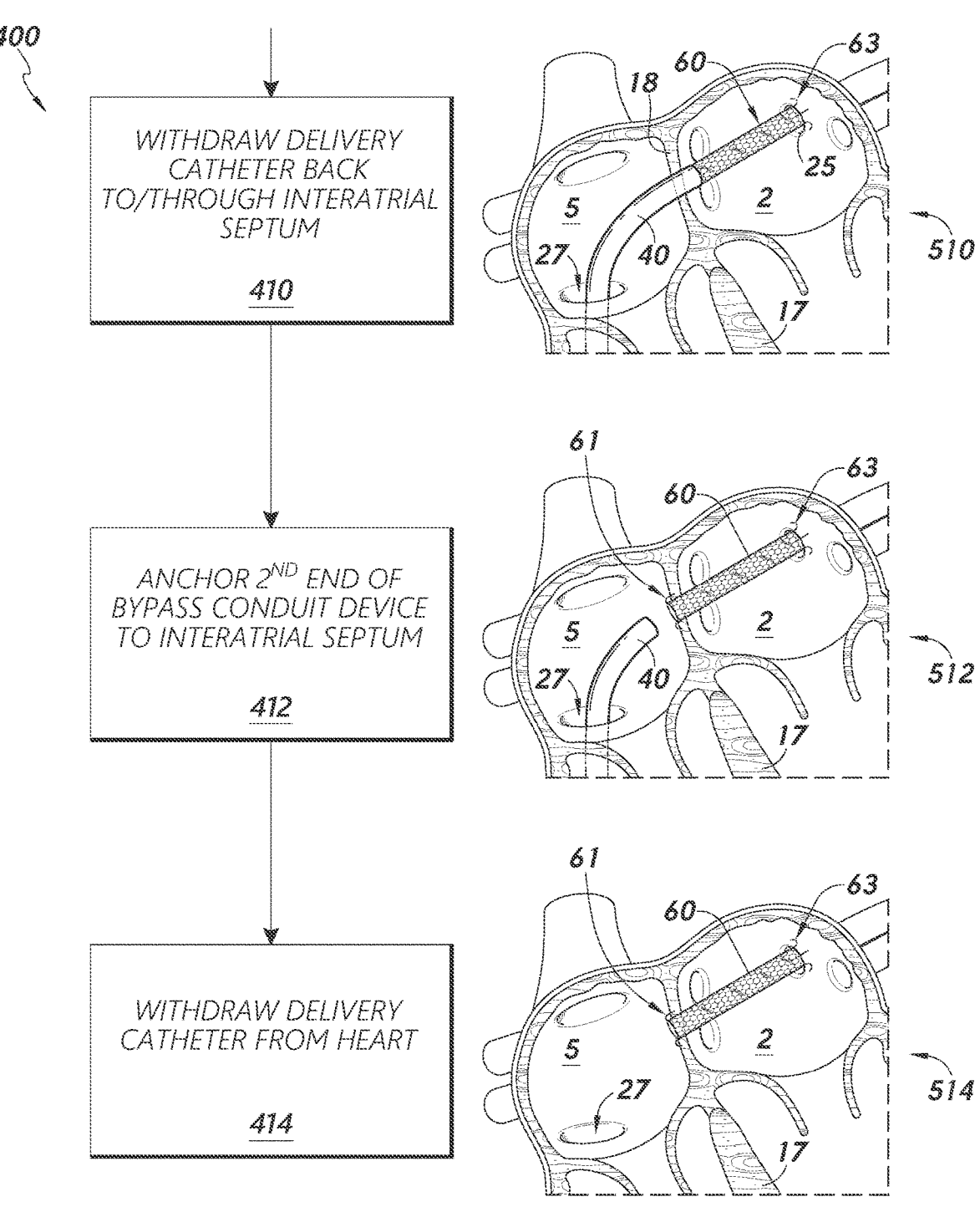
*400*
WITHDRAW DELIVERY
CATHETER BACK
TO/THROUGH INTERATRIAL
SEPTUM
<u>410</u>
ANCHOR 2^{ND} END OF
BYPASS CONDUIT DEVICE
TO INTERATRIAL SEPTUM
<u>412</u>
WITHDRAW DELIVERY
CATHETER FROM HEART
<u>414</u>
*FIG. 4-2*          *FIG. 5-2*

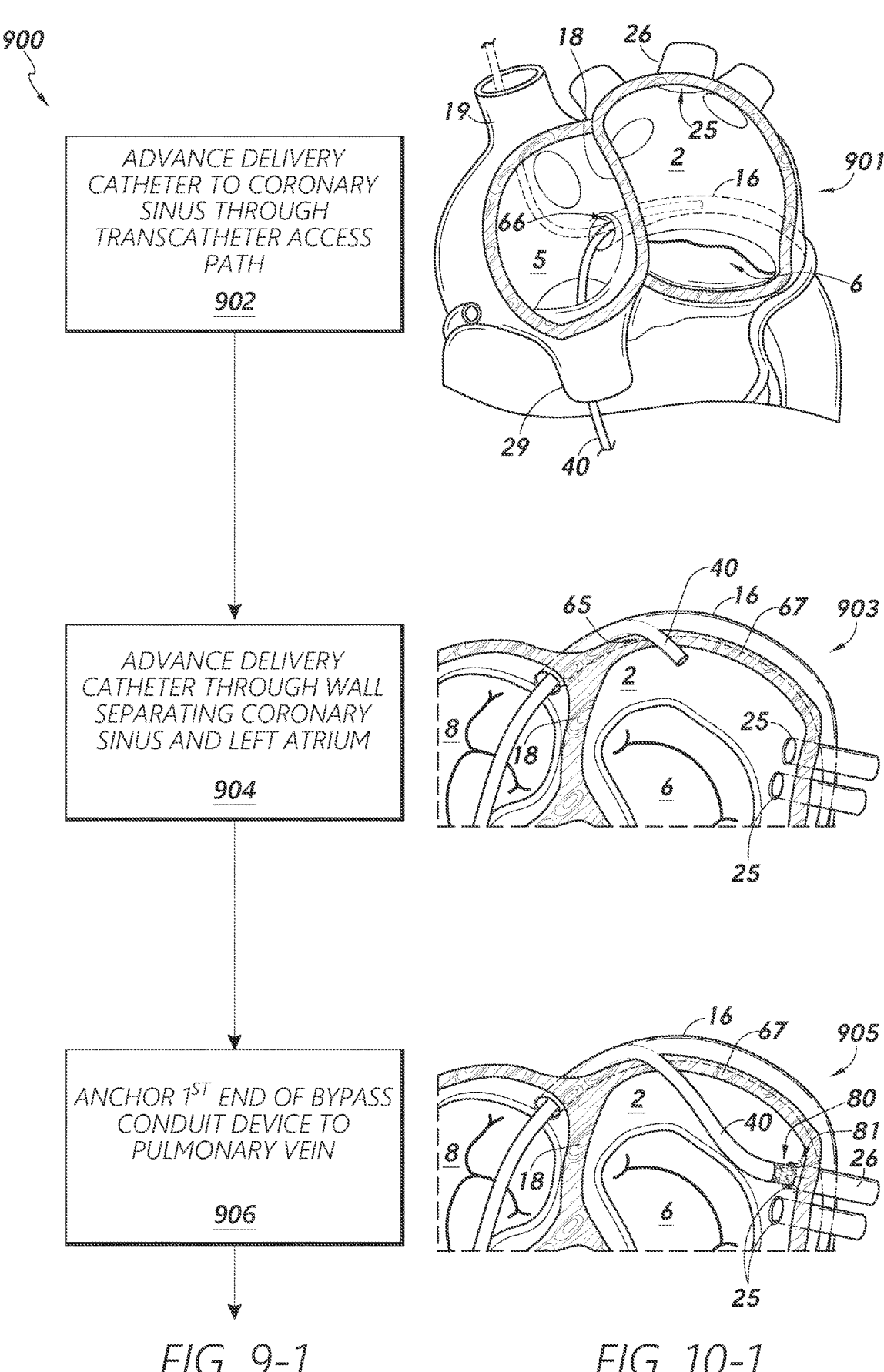
900
ADVANCE DELIVERY
CATHETER TO CORONARY
SINUS THROUGH
TRANSCATHETER ACCESS
PATH
902
ADVANCE DELIVERY
CATHETER THROUGH WALL
SEPARATING CORONARY
SINUS AND LEFT ATRIUM
904
ANCHOR 1$^{ST}$ END OF BYPASS
CONDUIT DEVICE TO
PULMONARY VEIN
906
FIG. 9-1                    FIG. 10-1

900

WITHDRAW DELIVERY
CATHETER BACK TO /
THROUGH CORONARY
SINUS WALL

908

ANCHOR 2$^{ND}$ OF BYPASS
CONDUIT DEVICE TO
CORONARY SINUS WALL

910

WITHDRAW DELIVERY
CATHETER FROM HEART

912

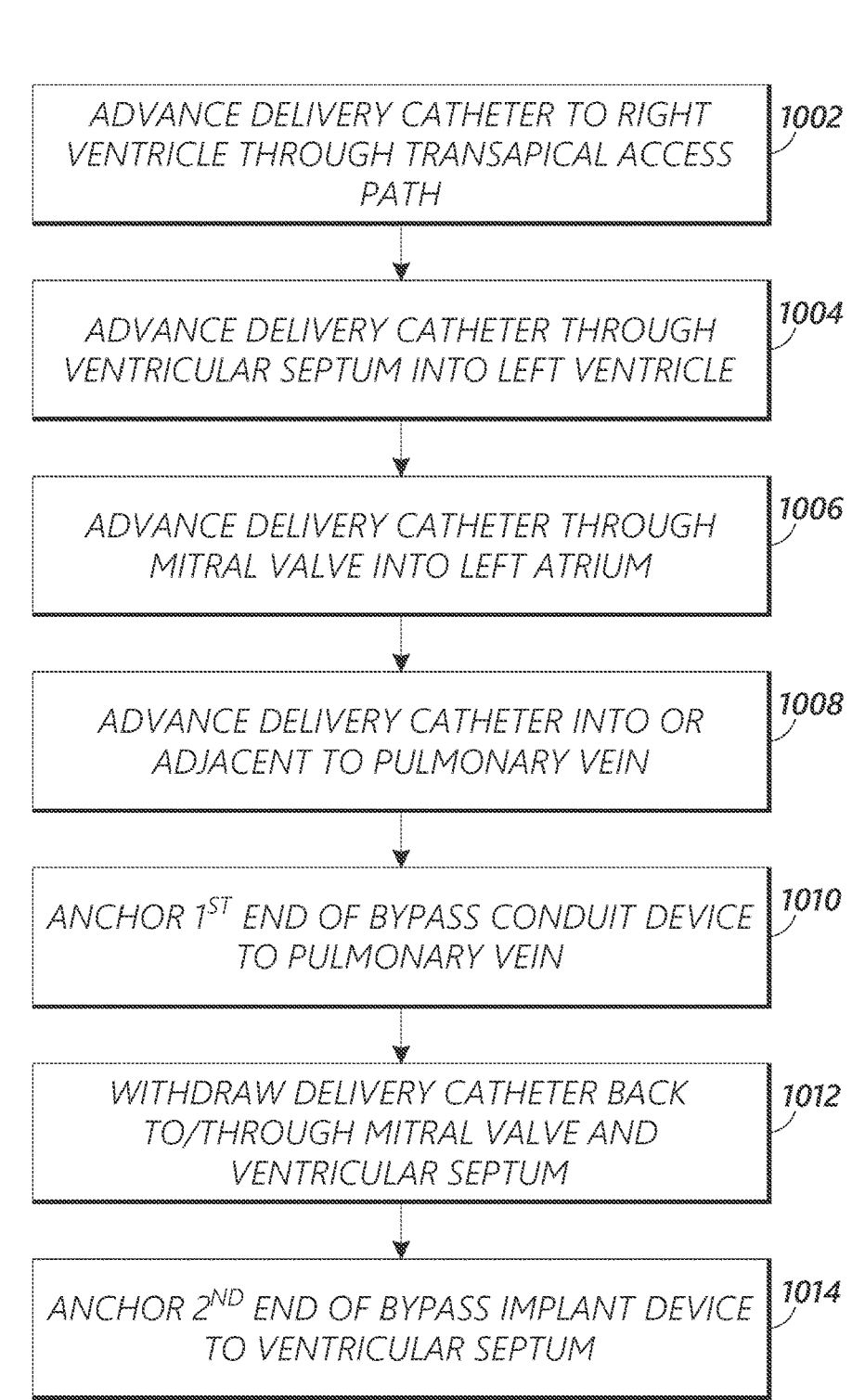

1000

ADVANCE DELIVERY CATHETER TO RIGHT VENTRICLE THROUGH TRANSAPICAL ACCESS PATH — 1002

ADVANCE DELIVERY CATHETER THROUGH VENTRICULAR SEPTUM INTO LEFT VENTRICLE — 1004

ADVANCE DELIVERY CATHETER THROUGH MITRAL VALVE INTO LEFT ATRIUM — 1006

ADVANCE DELIVERY CATHETER INTO OR ADJACENT TO PULMONARY VEIN — 1008

ANCHOR 1$^{ST}$ END OF BYPASS CONDUIT DEVICE TO PULMONARY VEIN — 1010

WITHDRAW DELIVERY CATHETER BACK TO/THROUGH MITRAL VALVE AND VENTRICULAR SEPTUM — 1012

ANCHOR 2$^{ND}$ END OF BYPASS IMPLANT DEVICE TO VENTRICULAR SEPTUM — 1014

FIG. 12

FLUID BYPASS CONDUIT FOR LEFT ATRIAL PRESSURE MANAGEMENT

RELATED APPLICATION

This application is a continuation of PCT International Patent Application Serial No. PCT/US2020/031139, filed May 1, 2020 and entitled FLUID BYPASS CONDUIT FOR LEFT ATRIAL PRESSURE MANAGEMENT, which claims priority based on U.S. Provisional Patent Application Ser. No. 62/860,623, filed Jun. 12, 2019 and entitled FLUID BYPASS CONDUIT FOR LEFT ATRIAL PRESSURE MANAGEMENT, the full disclosures of both of which are hereby incorporated by reference in their entireties.

BACKGROUND

Field

The present disclosure generally relates to the field of medical devices and procedures.

Description of Related Art

Certain physiological parameters associated with chambers of the heart, such as fluid pressure, can have an impact on patient health prospects. In particular, high cardiac fluid pressure can lead to heart failure and/or other complications in some patients. Therefore, reduction of pressure in certain chambers of the heart can improve patient health in some cases.

SUMMARY

Described herein are one or more methods and/or devices to facilitate reduction in left atrial pressure through channeling of fluid through the left atrium to thereby bypass the left atrium, at least in part.

In some implementations, the present disclosure relates to a method of managing left atrial pressure. The method comprises advancing a delivery catheter to a right atrium of a heart of a patient via a transcatheter access path, advancing the delivery catheter through an interatrial septum wall into a left atrium of the heart, deploying a distal end of a bypass fluid conduit from the delivery catheter, anchoring the distal end of the bypass fluid conduit to a pulmonary vein, withdrawing the delivery catheter through the interatrial septum wall, thereby exposing at least a portion of a medial segment of the bypass fluid conduit in the left atrium, anchoring a proximal end of the bypass fluid conduit to the interatrial septum wall, and withdrawing the delivery catheter from the heart.

The method may further comprise channeling blood from the pulmonary vein to the right atrium through the bypass fluid conduit. For example, said channeling the blood from the pulmonary sinus to the right atrium reduce left atrial pressure. In some embodiments, anchoring the distal end of the bypass fluid conduit to the pulmonary vein comprises embedding one or more barb tissue anchors associated with the distal end of the bypass fluid conduit into biological tissue associated with the pulmonary vein.

In some embodiments, the bypass fluid conduit comprises a self-expanding memory metal frame dimensioned to extend from the pulmonary vein to the interatrial septum, and an at least partially fluid-tight covering disposed over at least a portion of the frame. For example, anchoring the proximal end of the bypass fluid conduit to the interatrial septum wall can comprise expanding a wire coil anchor associated with the proximal end of the bypass fluid conduit, the wire coil having a diameter that is greater than a diameter of the frame. The method can further comprise anchoring the distal end of the bypass fluid conduit to another pulmonary vein using an anchor coupled to the distal end of the bypass fluid conduit by an arm member. In some implementations, the method further comprises inhibiting expansion of the left atrium using the bypass fluid conduit.

In some implementations, the present disclosure relates to a bypass fluid conduit comprising a self-expanding cylindrical frame dimensioned to extend longitudinally between a pulmonary vein and an interatrial septum, a covering disposed about at least a portion of the cylindrical frame, a first anchor associated with a first end portion of the cylindrical frame, and a second anchor associated with a second end portion of the cylindrical frame.

At least one of the first anchor and the second anchor may comprise a plurality of barbs configured to be embedded in biological tissue. In some embodiments, the first anchor is configured to anchor the first end portion of the cylindrical frame within the pulmonary vein and the second anchor is configured to hold the second end portion of the cylindrical frame within an opening in the interatrial septum. For example, in some implementations, the first anchor comprises a stent and the second anchor comprises a self-expanding wireworm having an expanded dimension that is greater than a diameter of the opening in the interatrial septum. The covering may be fluid-tight.

In some embodiments, the bypass fluid conduit further comprises a third anchor coupled to the first anchor. For example, the third anchor may comprise a clip form configured to clip the first anchor to an inside wall of a second pulmonary vein. In some embodiments, the first anchor and the third anchor are stent anchors and the first anchor is physically coupled to the third anchor via a bridge structure. The covering can have one or more apertures configured to allow fluid flow therethrough. In some embodiments, the cylindrical frame has an axially expandable portion configured to allow for axial contraction and expansion in order to change a length of the cylindrical frame when the cylindrical frame is in a deployed configuration.

In some implementations, the present disclosure relates to a bypass fluid conduit comprising a conduit form dimensioned to extend longitudinally between a pulmonary vein and a ventricular septum through a mitral valve. The conduit form comprises a first end portion, a second end portion, and a medial portion including a valve leaflet spacer portion configured to occupy a space between leaflets of a mitral valve. The bypass fluid conduit further comprises a first anchor associated with the first end portion of the conduit form and a second anchor associated with the second end portion of the conduit form.

The valve leaflet spacer portion can be associated with one or more reinforcement structures configured to reinforce the conduit form. In some embodiments, the one or more reinforcement structures are part of a covering that covers at least a portion of the medial portion of the conduit form. In some embodiments, the first anchor is configured to anchor the first end portion of the conduit form within the pulmonary vein and the second anchor is configured to hold the second end portion of the conduit form within an opening in the ventricular septum.

In some implementations, the present disclosure relates to a method of managing left atrial pressure. The method comprises advancing a delivery catheter to a right ventricle of a heart of a patient, advancing the delivery catheter through a ventricular septum wall into a left ventricle of the heart, advancing the delivery catheter through a mitral valve of the heart into a left atrium of the heart, deploying a distal end of a bypass fluid conduit from the delivery catheter, anchoring the distal end of the bypass fluid conduit to a pulmonary vein, withdrawing the delivery catheter through the mitral valve and the ventricular septum wall, thereby exposing at least a portion of a medial segment of the bypass fluid conduit in each of the left atrium and the left ventricle, anchoring a proximal end of the bypass fluid conduit to the ventricular septum wall, and withdrawing the delivery catheter from the heart.

The method may further comprise channeling blood from the pulmonary vein to the right ventricle through the bypass fluid conduit. In some implementations, the method may further comprise at least partially filling a gap between leaflets of the mitral valve using a valve spacer portion of the medial portion of the bypass fluid conduit. For example, channeling the blood and filling the gap can reduce both left atrial pressure and mitral regurgitation in the heart.

In some embodiments, anchoring the distal end of the bypass fluid conduit to the pulmonary vein comprises embedding one or more barb tissue anchors associated with the distal end of the bypass fluid conduit into biological tissue associated with the pulmonary vein. The bypass fluid conduit can comprise a self-expanding memory metal frame dimensioned to extend from the pulmonary vein to the interatrial septum and an at least partially fluid-tight covering disposed over at least a portion of the frame.

In some implementations, anchoring the proximal end of the bypass fluid conduit to the interatrial septum wall comprises expanding a wire coil anchor associated with the proximal end of the bypass fluid conduit, the wire coil having a diameter that is greater than a diameter of the bypass fluid conduit. The method can further comprise anchoring the distal end of the bypass fluid conduit to another pulmonary vein using an anchor coupled to the first anchor by an arm member.

In some implementations, the present disclosure relates to a method of managing left atrial pressure. The method comprises advancing a delivery catheter to a right atrium of a heart of a patient via a transcatheter access path, advancing the delivery catheter through an ostium of a coronary sinus of the heart into the coronary sinus, advancing the delivery catheter through an opening in a wall separating the coronary sinus from a left atrium of the heart, deploying a distal end of a bypass fluid conduit from the delivery catheter, anchoring the distal end of the bypass fluid conduit to a pulmonary vein, withdrawing the delivery catheter through the opening in the wall separating the coronary sinus from the left atrium, thereby exposing at least a portion of a medial segment of the bypass fluid conduit in the left atrium, anchoring a proximal end of the bypass fluid conduit to the wall separating the coronary sinus from the left atrium, and withdrawing the delivery catheter from the heart.

The method can further comprise channeling blood from the pulmonary vein to the coronary sinus through the bypass fluid conduit. Anchoring the distal end of the bypass fluid conduit to the pulmonary vein can comprise embedding one or more barb tissue anchors associated with the distal end of the bypass fluid conduit into biological tissue associated with the pulmonary vein. In some embodiments, the bypass fluid conduit comprises a self-expanding memory metal frame dimensioned to extend from the pulmonary vein to the wall separating the coronary sinus from the left atrium and an at least partially fluid-tight covering disposed over at least a portion of the frame. For example, anchoring the proximal end of the bypass fluid conduit to the wall separating the coronary sinus from the left atrium can comprise expanding a wire coil anchor associated with the proximal end of the bypass fluid conduit, the wire coil having a diameter that is greater than a diameter of the opening in the wall separating the coronary sinus from the left atrium. The method can further comprise anchoring the distal end of the bypass fluid conduit to another pulmonary vein using an anchor coupled to the first anchor by an arm member.

For purposes of summarizing the disclosure, certain aspects, advantages and novel features are described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 4-1 and 4-2 are a flow diagram illustrating a process for reducing left atrial pressure in accordance with one or more embodiments.

FIGS. 5-1 and 5-2 provide cross-sectional images of cardiac anatomy and certain devices corresponding to the process of FIG. 4 according to one or more embodiments.

FIGS. 9-1 and 9-2 are a flow diagram illustrating a process for reducing left atrial pressure in accordance with one or more embodiments.

FIGS. 10-1 and 10-2 provide cross-sectional images of cardiac anatomy and certain devices corresponding to the process of FIG. 9 according to one or more embodiments.

FIG. 12 is a flow diagram illustrating a process for treating high left atrial pressure and mitral regurgitation in accordance with one or more embodiments.

DETAILED DESCRIPTION

The headings provided herein are for convenience only and do not necessarily affect the scope or meaning of the claimed invention. The present disclosure relates to systems, devices, and methods for reducing left atrial pressure by bypassing one or more chambers of the heart.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The following includes a general description of human cardiac anatomy that is relevant to certain inventive features and embodiments disclosed herein and is included to provide context for certain aspects of the present disclosure. In humans and other vertebrate animals, the heart generally comprises a muscular organ having four pumping chambers, wherein the flow of blood between the pumping chambers is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

Figure 1:
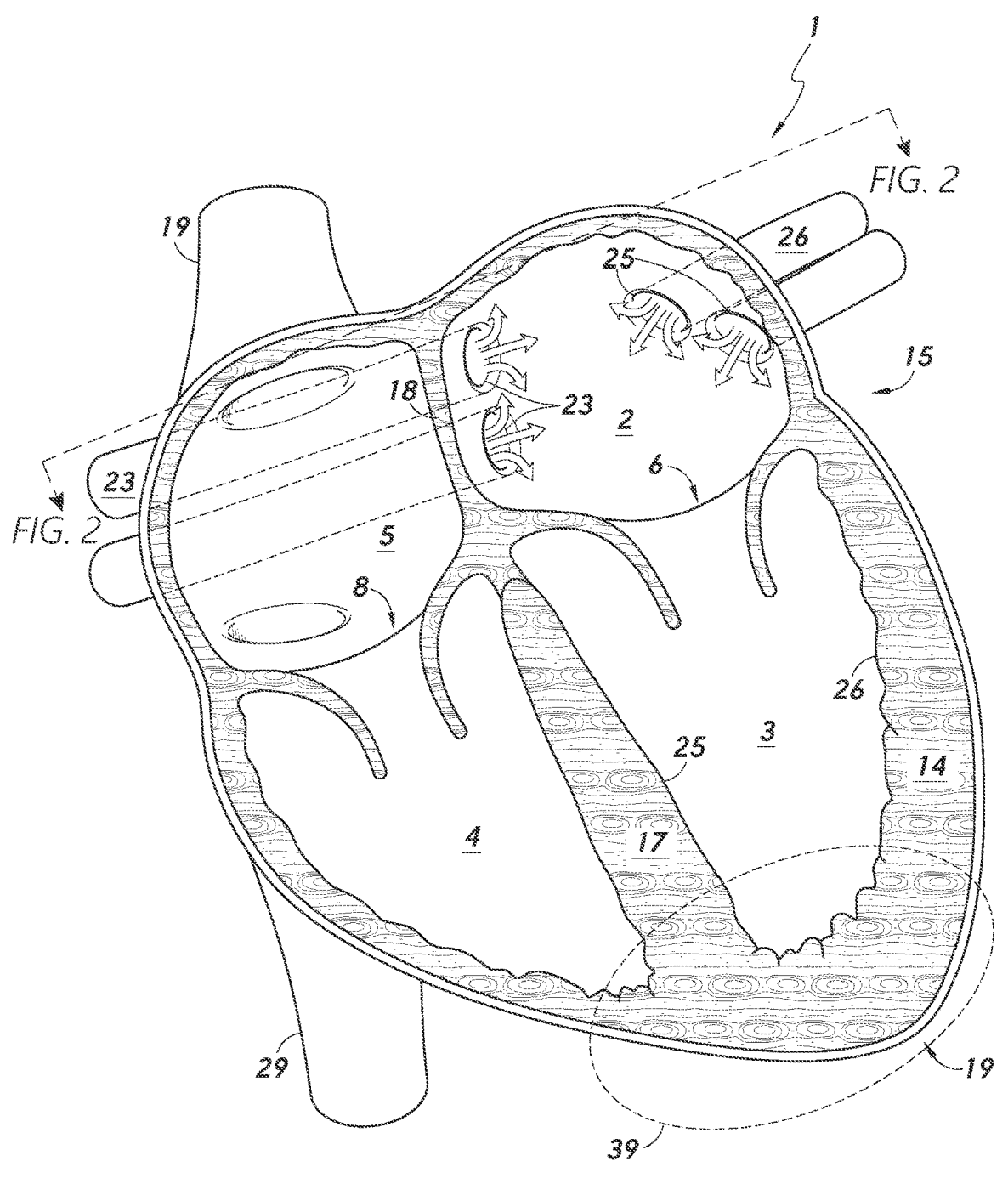
FIG. 1 provides a cross-sectional view of a human heart.
Figure 2:
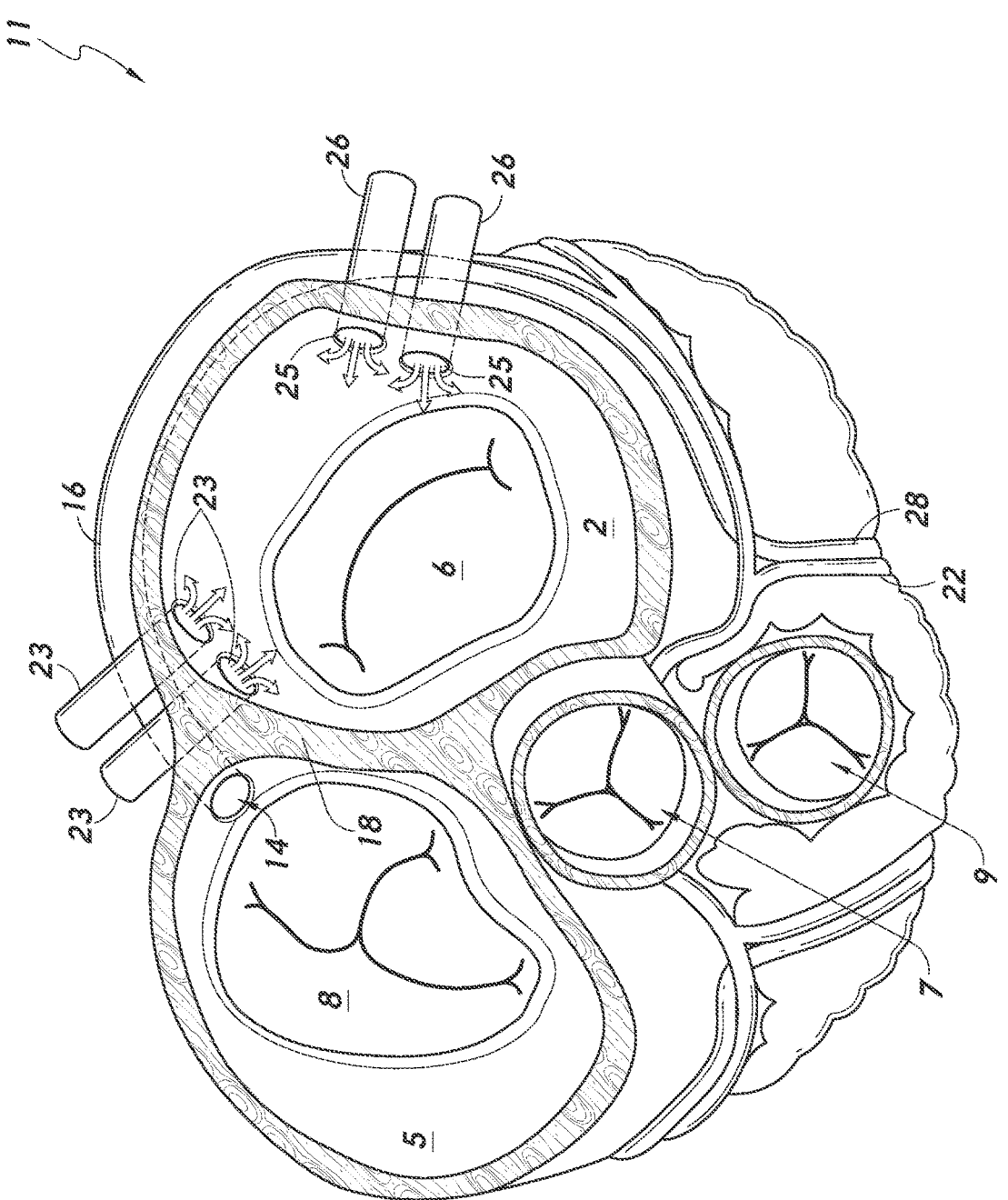
FIG. 2 shows a top-down atrial cross-sectional view of a human heart.

FIGS. 1 and 2 illustrate horizontal and vertical cross-sectional views, respectively, of an example heart 1 having various features/anatomy relevant to certain aspects of the present inventive disclosure. The heart 1 includes four chambers, namely the left ventricle 3, the left atrium 2, the right ventricle 4, and the right atrium 5. A wall of muscle, referred to as the septum, separates the left-side chambers from the right-side chambers. In particular, an atrial septum wall portion 18 (referred to herein as the "atrial septum," "interatrial septum," or "septum") separates the left atrium 2 from the right atrium 5, whereas a ventricular septum wall portion 17 (referred to herein as the "ventricular septum," "interventricular septum," or "septum") separates the left ventricle 3 from the right ventricle 4. The inferior tip 19 of the heart 1 is referred to as the apex and is generally located on the midclavicular line, in the fifth intercostal space. The apex 19 can be considered part of the greater apical region 39 identified in the drawings.

The left ventricle 3 is the primary pumping chamber of the heart 1. A healthy left ventricle is generally conical or apical in shape in that it is longer (along a longitudinal axis extending in a direction from the aortic valve 7 (not shown in FIG. 1) to the apex 19) than it is wide (along a transverse axis extending between opposing walls 25, 26 at the widest point of the left ventricle) and descends from a base 15 with a decreasing cross-sectional diameter and/or circumference to the point or apex 19. Generally, the apical region 39 of the heart is a bottom region of the heart that is within the left and/or right ventricular region but is distal to the mitral 6 and tricuspid 8 valves and disposed toward the tip 19 of the heart.

The pumping of blood from the left ventricle 3 is accomplished by a squeezing motion and a twisting or torsional motion. The squeezing motion occurs between the lateral wall 14 of the left ventricle 3 and the septum 17. The twisting motion is a result of heart muscle fibers that extend in a circular or spiral direction around the heart. When these fibers contract, they produce a gradient of angular displacements of the myocardium from the apex 19 to the base 15 about the longitudinal axis of the heart. The resultant force vectors extend at angles from about 30-60 degrees to the flow of blood through the aortic valve 7. The contraction of the heart is manifested as a counterclockwise rotation of the apex 19 relative to the base 15, when viewed from the apex 19. The contractions of the heart, in connection with the filling volumes of the left atrium 2 and ventricle 3, respectively, can result in relatively high fluid pressures in the left side of the heart at least during certain phase(s) of the cardiac cycle, the results of which are discussed in detail below.

The four valves of the heart aid the circulation of blood in the heart. The tricuspid valve 8 separates the right atrium 5 from the right ventricle 4. The tricuspid valve 8 generally has three cusps or leaflets and advantageously closes during ventricular contraction (i.e., systole) and opens during ventricular expansion (i.e., diastole). The pulmonary valve 9 separates the right ventricle 4 from the pulmonary artery 11 and generally is configured to open during systole so that blood may be pumped toward the lungs from the right ventricle 4, and close during diastole to prevent blood from leaking back into the right ventricle 4 from the pulmonary artery. The pulmonary valve 9 generally has three cusps/leaflets. The mitral valve 6 generally has two cusps/leaflets and separates the left atrium 2 from the left ventricle 3. The mitral valve 6 may generally be configured to open during diastole so that blood in the left atrium 2 can flow into the left ventricle 3, and close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The atrioventricular (i.e., mitral and tricuspid) heart valves are generally associated with a sub-valvular apparatus (not shown), including a collection of chordae tendineae and papillary muscles securing the leaflets of the respective valves to promote and/or facilitate proper coaptation of the valve leaflets and prevent prolapse thereof. The papillary muscles, for example, may generally comprise finger-like projections from the ventricle wall. Surrounding the ventricles (3, 4) are a number of arteries 22 that supply oxygenated blood to the heart muscle and a number of veins 28 that return the blood from the heart muscle to the right atrium 5 via the coronary sinus 16 (see FIG. 2). The coronary sinus 16 is a relatively large vein that extends generally around the upper portion of the left ventricle 3 and provides a return conduit for blood returning to the right atrium 5. The coronary sinus 16 terminates at the coronary ostium 14, through which the blood enters the right atrium.

The primary roles of the left atrium 2 are to act as a holding chamber for blood returning from the lungs (not shown) and to act as a pump to transport blood to other areas of the heart. The left atrium 2 receives oxygenated blood from the lungs via the pulmonary veins 23, 26. The oxygenated blood that is collected from the pulmonary veins 23, 26 in the left atrium 2 enters the left ventricle 3 through the mitral valve 6. In some patients, the walls of the left atrium 2 are slightly thicker than the walls of the right atrium 5. Deoxygenated blood enters the right atrium 5 through the inferior 29 and superior 19 venae cavae. The right side of the heart then pumps this deoxygenated blood into the pulmonary arteries around the lungs. There, fresh oxygen enters the blood stream, and the blood moves to the left side of the heart via a network of pulmonary veins ultimately terminating at the left atrium 2, as shown.

Heart Failure

Certain physiological conditions or parameters associated with the cardiac anatomy can impact the health of a patient. For example, congestive heart failure is a condition associated with the relatively slow movement of blood through the heart and/or body, which can cause the fluid pressure in one or more chambers of the heart to increase, particularly in the left side of the heart. As a result, the heart may not pump sufficient oxygen to meet the body's needs.

The various chambers of the heart may respond to pressure increases by stretching to hold more blood to pump through the body or by becoming relatively stiff and/or thickened. The walls of the heart can eventually weaken and become unable to pump as efficiently. In some cases, the kidneys may respond to cardiac inefficiency by causing the body to retain fluid. Fluid build-up in arms, legs, ankles, feet, lungs, and/or other organs can cause the body to become congested, which is referred to as congestive heart failure. Generally, left atrial pressure may be relatively highly correlated with risk of congestive heart failure. Furthermore, there may generally be a relatively strong correlation between increases in left atrial pressure and pulmonary congestion. Acute decompensated congestive heart failure is a leading cause of morbidity and mortality, and therefore treatment and/or prevention of congestive heart failure is a significant concern in medical care. Embodiments of the present disclosure can serve to treat and/or prevent congestive heart failure through reduction in left atrial pressure in patients suffering from high left atrial pressure.

Generally, increases in ventricular filling pressures associated with diastolic and/or systolic heart failure can occur prior to the occurrence of symptoms that lead to hospitalization. For example, cardiac pressure indicators may present weeks prior to hospitalization with respect to some patients. Therefore, reduction in left atrial and/or ventricular pressure in accordance with embodiments the present disclosure may advantageously be implemented as a preventative measure to reduce risks of hospitalization and/or the onset of heart failure.

Determination of high left atrial pressure may be made in any suitable or desirable way. Dyspnea represents a cardiac pressure indicator characterized by shortness of breath or the feeling that one cannot breathe well enough. Dyspnea may result from elevated atrial pressure, which may cause fluid buildup in the lungs from pressure back-up. Therefore, it may be desirable to implement certain left atrial pressure reduction solutions presented herein in response to dyspnea symptoms. Additionally or alternatively, left atrial pressure reduction in accordance with embodiments or the present disclosure may be implemented prior to manifestation of dyspnea symptoms and/or other symptoms/complications through direct and/or indirect pressure (e.g., left atrial pressure) monitoring and/or intervention. For example, left atrial pressure monitoring may be implemented using one or more sensors implanted or disposed in one or more chambers of the heart, such as within the left atrium. In some implementations, left atrial pressure may be derived or inferred through measurement of other chambers or vessels of the heart, which may serve as surrogates of left atrial pressure, such as measurements of pressure in one or more of the right atrium, right ventricle, pulmonary artery, and/or pulmonary artery wedge.

Left Atrial Pressure Reduction Using Fluid Bypass Conduit Implant Devices and Processes As described above, pressure elevation the left atrium may be correlated with certain heart failure conditions, as well as pulmonary congestion. Various medical conditions can lead to elevated left atrial pressure, including diastolic heart failure, systolic dysfunction of the left ventricle, and valve disease. Furthermore, both heart failure with preserved ejection fraction (HFpEF) and heart failure with reduced ejection fraction (HFrEF) can present with elevated left atrial pressure. These conditions can benefit from a reduction in left atrial pressure, which in turn generally reduces the systolic preload on the left ventricle. Reduction in left atrial pressure can also advantageously relieve pressure on the pulmonary circulation, reducing the risk of pulmonary edema, improving respiration and/or improving patient comfort. Embodiments of the present disclosure advantageously provide systems, devices, and methods for reducing left atrial pressure. In some implementations, left atrial pressure reduction is achieved by shunting an amount of blood flow, that otherwise would flow from the left atrium into the left ventricle and be ejected through the aortic valve during systole, through the left atrium to a flow path associated with the right side of the heart, such as through the interatrial septum or coronary sinus and into the right atrium. Disclosed herein are fluid bypass conduit devices, and methods of using the same, configured to provide such shunting through the left atrium.

Figure 3:
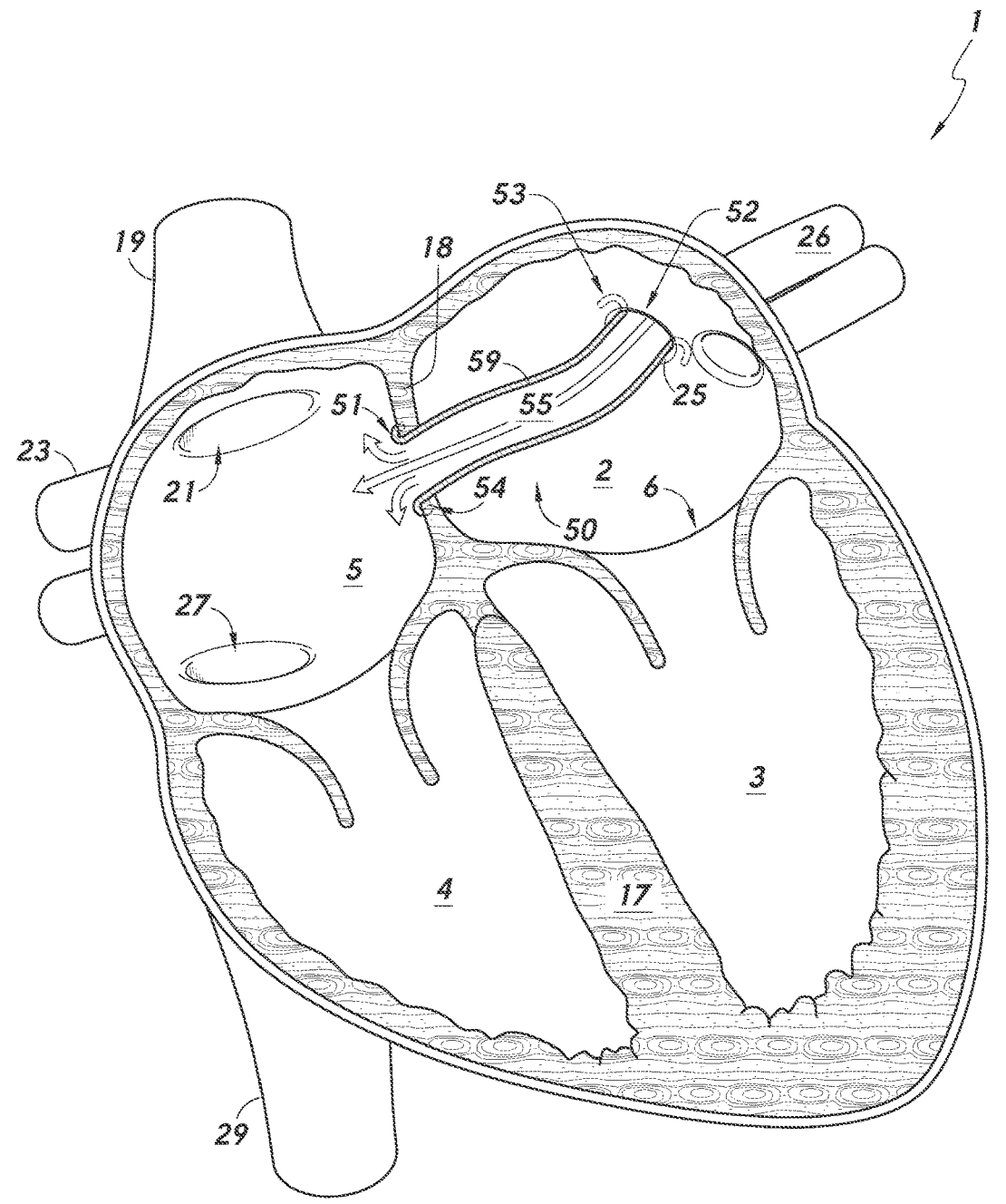
FIG. 3 illustrates a heart having a fluid bypass conduit device implanted therein in accordance with one or more embodiments.

FIG. 3 illustrates a heart 1 having a fluid bypass conduit device 50 implanted therein. Embodiments of the present disclosure relate to systems, devices, and methods for implanting fluid bypass conduit implant devices that may be similar in certain respects to the device 50 shown in FIG. 3, which may be configured to shunt or bypass blood flow from one area of the patient's vasculature to another. For example, embodiments of the present disclosure may advantageously involve shunting blood flow from an area in fluid communication with the left atrium 2, or other chamber or vessel associated with the left side of the heart, to the right side of the heart to thereby reduce left atrial pressure. Such methods may involve anchoring a first end 52 (e.g., distal end) of the fluid bypass conduit devices 50 on or in a pulmonary vein 26 and/or pulmonary vein ostium 25. The second end 54 (e.g., proximal end) of the fluid bypass conduit device 50 may be anchored in and/or through an interatrial septal wall 18 or ventricular septal wall 17 to provide fluid access from the pulmonary vein 26 and/or left atrium 2 into the right side of the heart, such as into the right atrium 5.

In some implementations, processes in accordance with the present disclosure involve implanting a fluid bypass conduit device such that a first end of the device is anchored in or to a pulmonary vein and/or pulmonary vein ostium, whereas the opposite end or portion of the implant device is anchored or secured to a wall or anatomy providing access to the coronary sinus. That is, the fluid bypass conduit device may advantageously provide fluid coupling between one or more pulmonary veins and the coronary sinus, which can allow for blood flow to drain from the left side of the heart into the right side of the heart (e.g., right atrium) via the coronary sinus.

As described above, the pulmonary veins 23, 26 transfer oxygenated blood from the lungs (not shown) to the heart 1. Generally, the largest pulmonary veins are the four main pulmonary veins 23, 26 (see FIGS. 1 and 2), two from each lung that drain into the left atrium 2. The pulmonary veins are part of the pulmonary circulation. Two main pulmonary veins emerge from each lung hilum, receiving blood from three or four bronchial veins apiece and draining into the left atrium 2. Generally, an inferior and superior main vein drains each lung, providing the four main veins shown in FIGS. 1 and 2. As shown in FIGS. 1 and 2, the left 26 and right 23 pulmonary veins generally enter the left atrium 2 via the posterior left atrial wall.

With further reference to FIG. 3, the fluid bypass conduit device 50 may be configured and/or shaped such that blood flow from the pulmonary veins is channeled at least partially within a lumen or channel 55 of the implant device 50 into the right atrium 5, thereby at least partially bypassing the left atrium 2 and/or ventricle 3. Attachment to the atrial septum wall 18 may be made in such a way as to allow for blood flow through the atrial septum 18 via the internal channel 55 of the bypass implant device 50. For example, a hole or opening may be formed in the septum 18 such that the implant bypass channel 55 passes through the septal wall 18.

The ends of the implant device 50 may be sutured or anchored to their respective target tissue, such as a pulmonary vein and/or septal wall, in any suitable or desirable way. As used herein, the term "pulmonary vein" may refer to a pulmonary vein ostium, vessel interior, and/or portion of left atrial tissue surrounding a pulmonary vein ostium. Furthermore, attachment or engagement with a pulmonary vein by a fluid bypass implant device and/or one or more anchor features associated therewith, as described herein, should be understood to relate to engagement or attachment of a fluid bypass implant device and/or associated anchor(s) with any tissue associated with the pulmonary vein, including at least a pulmonary vein ostium, vessel interior, and/or portion of left atrial tissue surrounding a pulmonary vein ostium. By anchoring the fluid bypass implant device 50 in the pulmonary vein 26 and/or ostium 25 associated therewith, blood flow from the pulmonary vein 26 can be channeled within the implant device into the right atrium 5, thereby bypassing the left atrium 2. The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled to, attached to, connected to, integrated with, embedded at least partially within, or otherwise physically related to the second feature, element, component, device, or member, whether directly or indirectly. Although certain embodiments are disclosed herein relating to anchoring of a fluid bypass implant device to a right and/or upper pulmonary vein, it should be understood the embodiments disclosed herein can involve anchoring or implanting of fluid bypass implant devices and/or anchor feature(s) thereof to any pulmonary vein or other vessel open to and/or associated with the left atrium or other chamber of the heart or body.

Attachment to the atrial septum wall 18 may be made in such a way as to allow for blood to flow through the atrial septum 18 via the internal channel 55 of the bypass conduit device 50. For example, a hole or opening may be formed in the septum 18 such that the implant bypass channel 55 passes through the septal wall 18. With the conduit device 50 engaged with a single pulmonary vein 26, only a fraction of the total blood supplied to the left atrium 2 via the pulmonary veins may be re-routed to the right side of the heart 1. In some implementations, engagement with one pulmonary vein may divert approximately 25% of the total oxygenated blood flow from the lungs to the left atrium 5 and/or left ventricle 4.

Although a single pulmonary vein is shown in FIG. 3 as being engaged by the device 50, in some embodiments, the device may couple to more than one pulmonary vein, or more than one fluid bypass conduit implant device may be employed, to provide increased pressure reduction. For example, the device 50 may have a manifold-type configuration, wherein multiple distal channels of the device are combined together and directed towards the opening in the septal wall.

In some embodiments, the implant device 50 may comprise a tubular, or partially-tubular member or portion 59 having one or more anchors associated with respective ends thereof. The tubular section 59 may advantageously comprise a self-expanding tubular structure. Furthermore, the fluid bypass conduit 50 may comprise a fluid-tight covering around at least a portion of the tubular component (e.g., internal frame) 59. In some embodiments, the tubular portion 59 does not include an internal frame. One end 52 (e.g., distal end) of the fluid bypass conduit 50 may be implanted in the pulmonary vein 26 and/or pulmonary vein ostium 25. An opposite end 54 (e.g., proximal end) of the conduit device 50 may be implanted through the interatrial septal wall 18 to provide fluid access through the channel 55 of the conduit device 50 from the pulmonary vein 26 into the right atrium 5. In some embodiments, rather than providing fluid access through the interatrial septum wall 18, the conduit device 50 may be implanted in the pulmonary vein 26 and/or pulmonary vein ostium 25, whereas the opposite end of the device 50 may be implanted in a wall of the left atrium in a position to provide fluid access through the channel 55 into the coronary sinus 16 (see FIGS. 2 and 10).

The fluid bypass conduit device 50 may act as a bypass channel connecting or tapping from one or more of the four pulmonary veins and redirecting or shunting blood flow from the vein(s) directly into the right atrium 5 through the septal wall 18. By bypassing blood flow from one or more pulmonary veins to the right atrium, fluid that otherwise would fill the left atrium and increase fluid pressure therein can be channeled instead into the right atrium, thereby reducing left atrial pressure, and accordingly reducing risk of heart failure and/or other health complications.

The anchor feature(s) 53 associated with the distal end 52 of the fluid bypass conduit device 50 may be any type of tissue anchor or engagement feature(s). For example, in some embodiment, the anchor feature(s) 53 are friction-fit, tissue-engagement anchors, such as one or more self-expanding stent features. The anchor feature(s) 51 associated with the proximal end 54 of the fluid bypass conduit device 50 may be similar or different type(s) of anchor feature(s) than the anchor feature(s) 53. For example, the anchor feature(s) 51 may comprise one or more wire and/or coil forms having a width or diameter dimension greater than the opening in the septum 18 and configured to prevent the proximal end 54 of the device 50 from being drawn or pulled through the opening into the left atrium 2.

The fluid bypass conduit device 50 can inhibit undesirable expansion or dilation of the left atrium 2 once it is implanted in accordance with some implementations. That is, the fluid bypass conduit device 50 can advantageously serve to prevent the left atrium 2 and/or other chamber of the heart 1 from dilating or expanding due to undesirable enlargement. For example, the bypass fluid conduit 50 (e.g., a metal frame thereof (see frame 37 of FIG. 6) and/or other component of the bypass fluid conduit) can act as a tensioning device to prevent possible enlargement of the left atrium. Some embodiments include a self-expanding memory metal frame and/or an at least partially fluid-tight covering. Although a variety of features of the fluid bypass conduit device 50 are shown in FIG. 3, it should be understood that features can be implemented independently of any of the other features shown and described.

Figures 1, 4, 5:
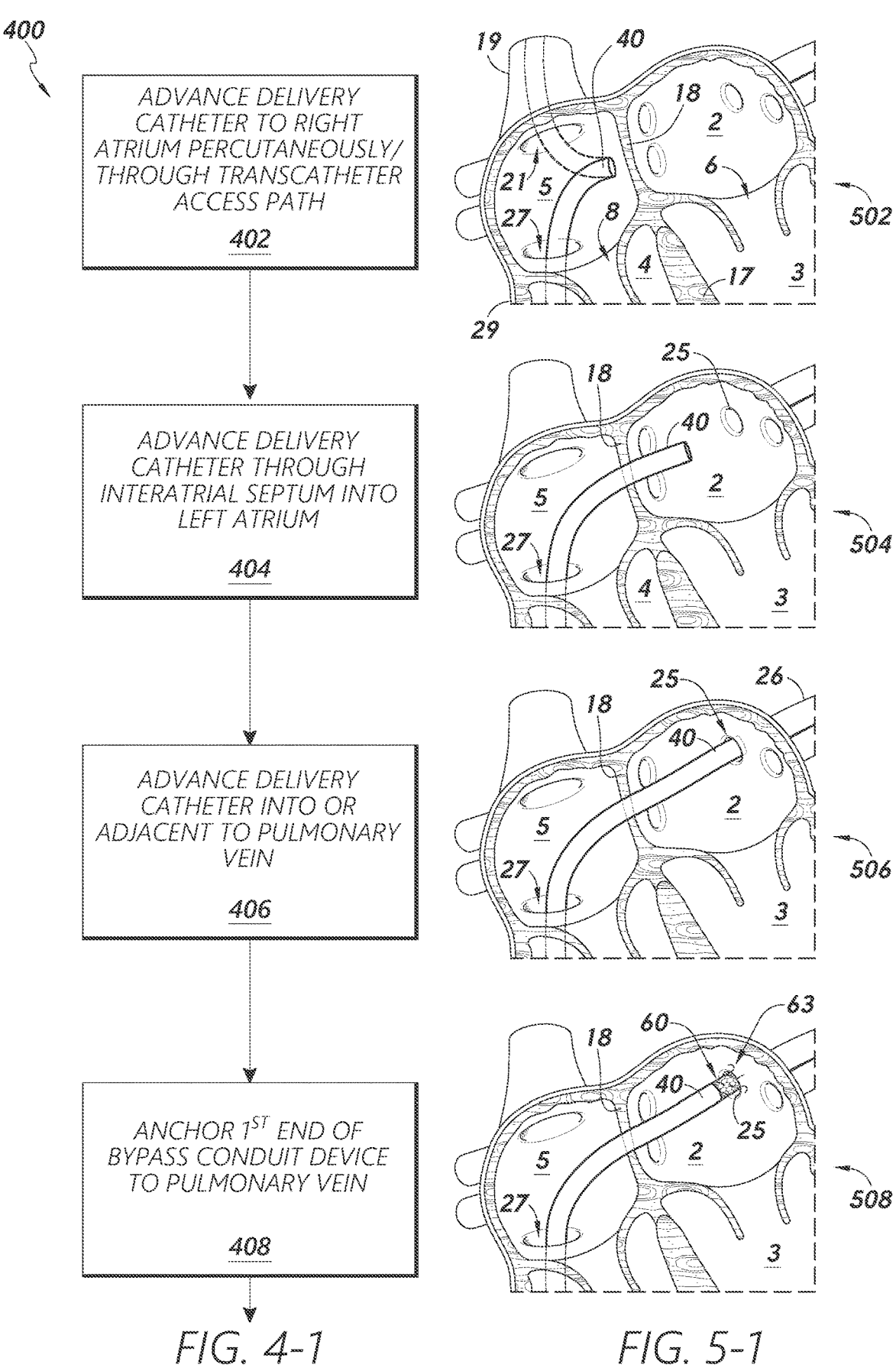

FIG. 4 is a flow diagram illustrating a process 400 for reducing left atrial pressure using one or more fluid bypass conduit implant devices in accordance with one or more embodiments of the present disclosure. FIG. 5 shows certain cross-sectional images of cardiac anatomy and certain devices associated with the process 400 of FIG. 4 to illustrate aspects of the process 400 according to one or more implementations thereof.

At block 402, the process 400 involves advancing a delivery catheter and/or sheath 40 to a right atrium 5 of a patient percutaneously through a transcatheter access path. For example, access to the right atrium 5 may be made via the inferior vena cava 29 or superior 19 vena cava. For example, as shown in image 502, the delivery catheter 40 may be advanced to the right atrium 5 through an inlet opening 21 from the superior vena cava 19 or through the inlet opening 27 from the inferior vena cava 29. The terms "catheter" and "sheath" are used herein according to their broad and ordinary meanings and may refer to any type of tube suitable for insertion in the body. "Catheter" and "sheath" may be used substantially interchangeably is some contexts herein.

Although not shown in FIG. 5 or described in detail herein for clarity purposes, processes for deploying and/or implanting fluid bypass conduit devices in accordance with embodiments of the present disclosure may involve introducing a guidewire through the relevant access path prior to deployment of the delivery catheter 40. Once the guidewire provides a path, an introducer sheath (not shown) may be routed along the guidewire and into the patient's vasculature. For example, the introduction of the introducer may be achieved with the use of a dilator. The introducer sheath may advantageously provide a hemostatic valve to prevent blood loss.

The delivery catheter 40 may contain therein a fluid bypass conduit device 60 in accordance with embodiments of the present disclosure. At block 404, the process 400 involves advancing the delivery catheter 40 through the interatrial septum 18 to access the left atrium 2. For example, the delivery catheter 40 may function to form and prepare an opening in the atrial septum 18. In some implementations, a separate placement or delivery catheter can be used for delivery of the fluid bypass implant device. In other embodiments, the delivery catheter may be used as the both the puncture preparation and fluid bypass conduit device placement catheter. In the present application, the term "delivery catheter" is used according to its broad and ordinary meaning and can refer to a catheter or introducer with one or both of these functions. At block 406, the process 400 involves advancing the delivery catheter 40 into or adjacent to a pulmonary vein or pulmonary vein ostium 25.

At block 408, the process 400 involves anchoring a distal end of the fluid bypass conduit device 60 transported within the delivery catheter 40 to the pulmonary vein 26 and/or pulmonary vein ostium 25. The conduit device 60 can comprise a generally tubular body or sleeve defining a lumen. The distal end of the conduit device 60 may serve as a fluid inlet. The distal end of the conduit device 60 may be associated with one or more anchoring features 63, which may be used to anchor the conduit device 60 to the pulmonary vein 26. The anchor feature(s) 63 may comprise, for example, one or more barb- or corkscrew-type tissue anchors and/or a stent form for anchoring to and/or in the pulmonary vein 26.

The bypass fluid conduit device 60 may be implanted at or in the pulmonary vein 26, 25 in such a way as to effectively fluid-seal the target pulmonary vein. Alternatively, the distal end of the conduit device 60 may be implanted or anchored at the pulmonary vein or pulmonary vein ostium in such a way as to include gaps or spaces around a periphery of the conduit device 60 through which blood may flow. Such gaps or spaces may be intentionally and/or deliberately allowed or implemented or may result naturally from imperfect sealing or anchoring of the conduit device 60. Although the process 400 is described as involving first implanting the conduit device 60 in the pulmonary vein and secondly implanting the proximal end of the device 60 in the septum 18, in some implementations, the fluid bypass conduit device 60 may first be anchored to the septum 18, after which one or more of the pulmonary veins may be identified as providing a desired or ideal output or reduction in pressure, and such identified vein(s) may be coupled to the conduit device 60.

As described above, four separate pulmonary veins, two from the right and two from the left, may channel blood into the left atrium 2. Therefore, each of the pulmonary veins individually contributes only a portion of the total inlet flow into the left atrium 2. In some embodiments, the target pulmonary vein 26 may be selected to optimize an amount of blood flow shunted from the left side of the heart to the right. For example, the process 400 may involve selecting a desired one or number of pulmonary veins designed to provide the desired portion of the inlet blood flow from the lungs through the bypass conduit device 60. In some patients, a fluid bypass conduit device coupled to a single pulmonary vein may channel approximately 25% of the inlet blood flow into the left atrium 2 to the right side of the heart. Therefore, left atrial pressure may be reduced by approximately 25%, or some other percentage between 0-25%, by implanting a fluid bypass conduit device in accordance with embodiments of the present disclosure between a single pulmonary vein and the right atrium or ventricle via a septal or atrial wall.

At block 410, the process 400 involves withdrawing the delivery catheter 40 back to and/or through the interatrial septum 18, thereby deploying a medial channel portion of the fluid bypass conduit 60 and exposing the same in the left atrium 2. The bypass conduit device 60 may advantageously be at least partially self-expanding, and may include a jacket or cover, which may comprise thin PTFE material or similar, or biological tissue. The medial portion of the conduit device 60 can comprise an at least partially rigid frame, which may comprise an expandable laser-cut metal frame and/or one or more annular hoops covered by a sleeve or covering. The frame can be generally cylindrical with respect to a cross-sectional shape thereof over at least a longitudinal portion of the conduit form of the device 60, as shown in various figures and described in certain contexts herein. The medial portion of the conduit device 60 may advantageously be at least partially flexible and may be pre-formed into a desired (e.g., at least partially curved) shape. The conduit device 60 can be advanced from the delivery catheter by pushing the conduit device 60 out of the delivery catheter 60 and/or retracting the delivery catheter 40 relative to the conduit device 60. In some implementations, a pusher device extending axially through at least a portion of the delivery catheter 40 may be used to assist in deploying the conduit device 60 from the catheter.

At block 412, the process 400 involves anchoring a proximal end of the fluid bypass conduit device 60 to the interatrial septum 18, such that the internal fluid channel of the conduit 60 provides a pathway from the pulmonary vein 26 through the atrial septum 18 and into the right atrium 5. The anchor feature(s) 61 associated with the proximal end of the conduit device 60 may be any type of anchor features, including expanding coils or arms, or barb-type anchors configured to embed in the tissue of the septal wall 18. Although certain portions of the description herein are focused on shunting through the atrial septum 18, it should be understood that in some embodiments shunting may be through a left atrial wall between the left atrium 2 and the coronary sinus, wherein shunting to the right side of the heart is via the coronary sinus and Thebesian valve into the right atrium 5

At block 414, the process 400 involves withdrawing the delivery catheter 40 from the heart of the patient, thereby leaving the fluid bypass implant device 60 implanted as shown in image 514. Due to the generally higher-pressure state in the left side of the heart compared to the right side of the heart, fluid back flow from the right atrium to the left side of the heart may generally not occur in the steady-state implanted condition. With the delivery catheter withdrawn, the fluid bypass conduit device 60 can advantageously provide shunting from the left side of the heart to the right side of the heart, as described above.

Figure 6:
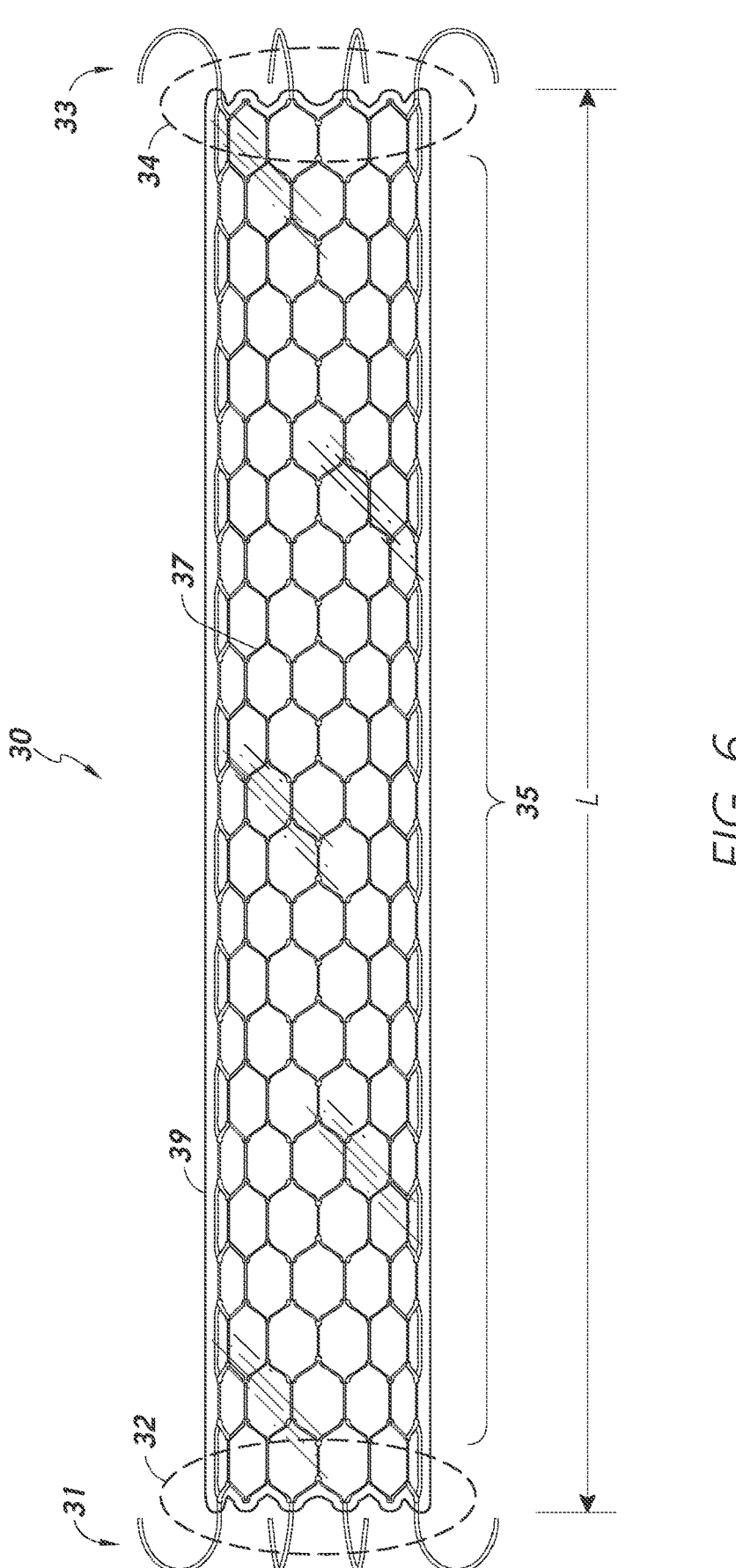
FIG. 6 illustrates an embodiment of a fluid bypass conduit device in accordance with one or more embodiments.

FIG. 6 illustrates an embodiment of a fluid bypass conduit device 30 in accordance with one or more embodiments. The conduit device 30 may be a self-expanding implant device in accordance with embodiments disclosed herein. In some embodiments, the fluid bypass conduit device 30 comprises a self-expanding stent or frame component 37, which may be shaped and configured to form a conduit, such as a cylindrical-cross-sectional conduit, as described herein. Although self-expanding frames and conduits are described herein, in some embodiments, a fluid bypass conduit device may be balloon-expandable or may not require expansion after deployment from the delivery catheter. Furthermore, although transcatheter processes are described herein, in some embodiments, access to the left ventricle may be implemented via surgical access or minimally invasive access (e.g., transthoracic access).

Opposite ends 32, 34 of the conduit formed by the frame 37 can be coupled to and/or otherwise associated with one or more anchor components 31, 33, respectively. The device 30 shown in FIG. 6 is illustrated in an expanded configuration. In a compressed or collapsed configuration, the device 30 may be transportable to a target implantation location using a catheter via femoral or jugular access and crossing through the interatrial septum or other path to the left atrium. The image of FIG. 6 shows barb-type tissue anchors 31, 33. However, it should be understood that any types of anchors may be utilized in connection with fluid bypass conduit devices in accordance with embodiments of the present disclosure.

Although certain embodiments are disclosed herein showing a single fluid bypass conduit device and/or a fluid bypass conduit device implanted in only a single pulmonary vein, in some implementations, a fluid bypass conduit device may be implanted in fluid communication with more than one pulmonary vein. For example, such implementations may utilize two separate conduit devices, or may utilize a single conduit device having a plurality of distal conduit openings/inlets for implantation in more than one pulmonary vein. Additional pulmonary veins may be tapped in order to provide the desired pressure-reduction functionality.

The tissue anchors 31, 33 shown in FIG. 6, as well as those described in connection with other embodiments of the present disclosure, may be any suitable or desirable types of tissue anchors. For example, in some embodiments, a tissue anchor associated with a fluid bypass conduit device comprises a pre-shaped wireform, such as a loop, coil, spiral, or the like, which may be configured to assume a relatively wide tissue anchor profile once deployed from the delivery catheter. Other types of tissue anchors that may be used include, but are not limited to, tension-fit or resistance-fit tissue anchors, such as stents or the like, barb-type tissue anchors, which may incorporate tip features configured to resist withdrawal of the anchor tip(s) from tissue in which it is embedded following embedding, corkscrew-type tissue anchors, and/or other types of tissue anchors that may or may not be known in the art.

As described in detail herein, the fluid bypass conduit device 30 may advantageously be dimensioned to have a length L sufficient to traverse the left atrium of the patient. For example, the fluid bypass conduit device 30 may have a length of approximately 2-5 cm. In some embodiments, the length L of the device 30 is approximately 4 cm. In some embodiments, the conduit device 30 is configured to have a variable length, wherein the length of the conduit may adjust or flex in response to contraction of the atrium. That is, the fluid bypass conduit device 30 may advantageously be configured with self-expansion characteristics allowing for expansion and/or contraction of the atrium being absorbed by the frame 37 and/or other components of the device 30. In some embodiments, the fluid bypass conduit device 30 advantageously includes a covering 39, which may be disposed within or without the frame 37, and may be at least partially fluid-tight, to thereby facilitate funneling or channeling of blood flow through the medial portion/segment 35 of the conduit device 30. Although a variety of features of the fluid bypass conduit device 30 are shown in FIG. 6, it should be understood that such features can be implemented independently of any of the other features shown and described.

Figure 7:
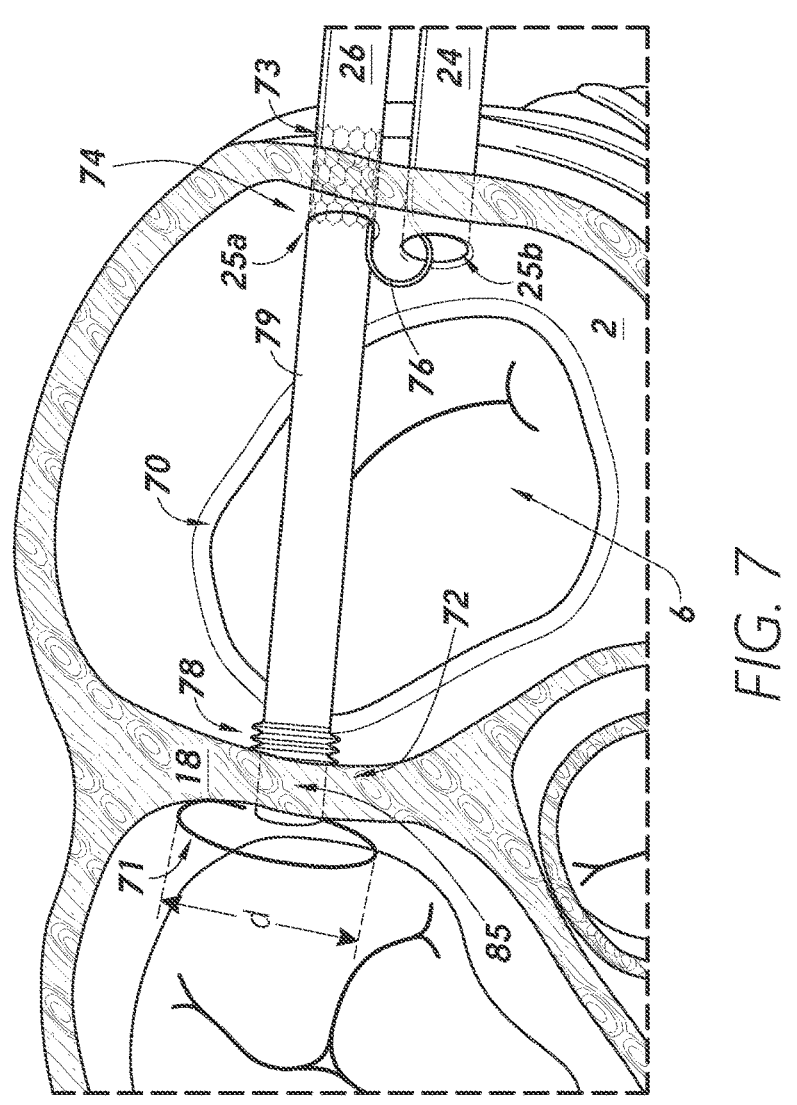
FIG. 7 shows a top-down view of a left atrium having implanted therein a fluid bypass conduit device in accordance with one or more embodiments.

FIG. 7 shows a top-down view of a left atrium 2 having implanted therein a fluid bypass conduit device 70 in accordance with one or more embodiments of the present disclosure. The conduit device 70 shown in FIG. 7 includes various features that may be incorporated in any of the disclosed embodiments. For example, the conduit device 70 includes an accordion-type shock absorber feature 78, which may be part of, or incorporated in, one or more of an internal frame and/or covering 79 of the conduit device 70, as described in detail herein. The feature can generally be configured to axially contract and/or allow for axial contraction of the conduit device 70. For example, the feature 78 may comprise a plurality of pleated layers that may be integrated with the covering 79 and allow for longitudinal expansion and contraction of the conduit device 70. The shock-absorber feature 78 may advantageously be compressible to accommodate reduction in longitudinal length of the conduit in connection with contraction of the atrium 2.

In some embodiments, the conduit device 70 may comprise one or more holes or apertures in the covering 79 to allow for fluid outflow into the atrium 2. For example, some embodiments may allow for selective opening formation in the covering 79 and/or one or more other components of the conduit device 70 to adjust the pressure reduction effect of the conduit device 70. That is, the conduit device 70 may allow for adjustable shunting functionality. For example, in some embodiments, the conduit device 70 may comprise adjustable shunting mechanisms, such as certain holes or apertures in the covering and/or other features of the conduit device 70 that may become more or less offset with respect to one another in an overlapping configuration in response to increased pressure or other modifications of the device 70 or environment. Therefore, in some embodiments, the increased pressure within (or without) the conduit 70 can results in larger opening(s) in the covering 79 and/or other components of the device 70, such that additional blood may flow from the conduit 70 into the atrium 2. In some implementations, axial rotation implemented on the conduit device 70 and/or one or more components thereof may serve to restrict or open blood flow, thereby modifying the characteristics of the conduit device 70. Adjustable shunting features may comprise any form or type of mechanism that serves to make the conduit 70 and/or one or more components thereof more or less porous to blood flow. In some embodiments, the conduit device 70 may have compliance characteristics to allow for expansion thereof under certain high-pressure conditions.

As described in detail herein, tissue-anchoring components or portions of a fluid bypass conduit device in accordance with embodiments of the present disclosure may comprise any suitable or desirable form or mechanism, including any known tissue-anchoring devices or mechanisms. In the illustrated embodiment of FIG. 7, the conduit device 70 advantageously includes an expandable (e.g., self-expanding and/or memory metal) anchor 71 associated with a proximal 72 (or distal 74) end portion of the conduit device 70. For example, the expandable anchor 71 may have a diameter d in an expanded configuration that is greater than one or both of a diameter of the opening 85 in the atrial septum 18 and the diameter of the conduit device 70, such that the anchor 71 retains the conduit device 70 in place and prevents the proximal end 72 of the conduit device 70 from being pulled through the opening 85 in the atrial septum 18 into the left atrium 2.

One end, such as the distal end 74, of the conduit device 70 may be associated with a tension/resistance anchor, such as a stent 73 or similar structure or device. For example, the stent 73 may be expanded within a pulmonary vein 26, as shown. In some embodiments, the conduit device 70 may be anchored to more than one pulmonary vein. For example, an anchor 73 or distal and portion 74 of the conduit device 70 may be associated with a clip or arm feature 76, which may be configured to be disposed within, or otherwise anchored to, an adjacent pulmonary vein 24 and/or ostium thereof 25*b*, such as being clipped to an inside wall of the pulmonary vein 24, as shown. The clip or arm member 76 may be configured to provide inward radial force with respect to the axis of the conduit device 70 to thereby provide additional anchoring of the conduit device 70 to the second pulmonary valve 24 as well.

Figure 8:
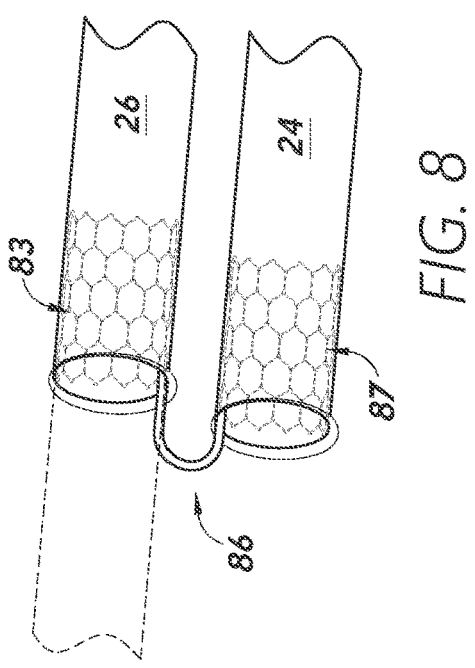
FIG. 8 shows conduit anchors engaged in a plurality of pulmonary veins in accordance with one or more embodiments.

In some embodiments, anchoring between adjacent pulmonary veins may be accomplished using a tension/resistance anchor 87 in the adjacent pulmonary vein 24, as shown in FIG. 8. In FIG. 8, a first anchor stent 83 is deployed in a first pulmonary vein 26, wherein the stent 83 is associated with and/or coupled to a distal end portion of a fluid bypass conduit device (not shown) in accordance with embodiments of the present disclosure. The first anchor 83 is coupled to a secondary anchor 87 deployed within the adjacent pulmonary vein 24, wherein the first and second anchors 83, 87 are coupled to one another by a bridge or arm member 86, which may be at least partially rigid and/or flexible. In some embodiments, the bridge/arm member 86 has shape memory and/or resilience characteristics that introduce a force on the anchors 83, 87 towards one another. Either or both of the anchors 83, 87 may be self-expanding stents. Implementation of a secondary anchor 87 and bridge/arm member 86 may serve to provide improved anchoring for a fluid bypass conduit device in accordance with embodiments of the present disclosure. Although a variety of features shown in FIGS. 7 and 8, it should be understood that such features can be implemented independently of any of the other features shown and described.

Fluid Bypass Through the Coronary Sinus

Figures 2, 9, 10:
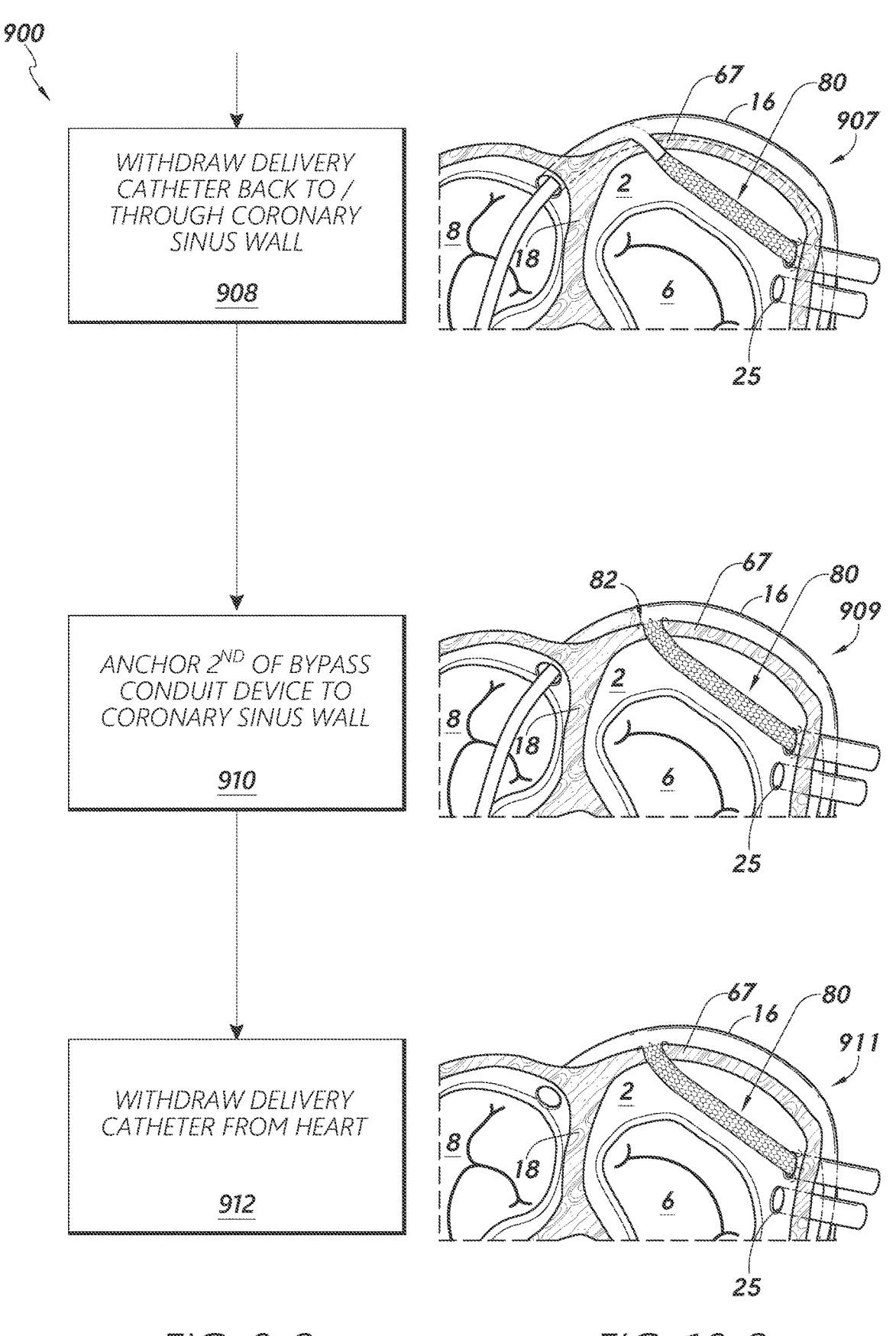

As an alternative to using a fluid bypass conduit device to fluidly couple a pulmonary vein to the right side of the heart through the interatrial septum, principles disclosed herein are applicable to other implantation configurations, including fluidly coupling one or more pulmonary veins to the right side of the heart via the coronary sinus. FIG. 9 is a flow diagram illustrating a process 900 for reducing left atrial pressure using one or more fluid bypass conduit implant devices configured to fluidly couple one or more pulmonary veins to the coronary sinus in accordance with one or more embodiments of the present disclosure. FIG. 10 shows certain cross-sectional images of cardiac anatomy and certain devices associated with the process 900 of FIG. 9 to illustrate aspects of the process 900 according to one or more implementations thereof.

At block 902, the process 900 involves advancing a delivery catheter 40 to a coronary sinus 16 of a heart of a patient via a transcatheter access path. As described above, various access pathways may be utilized for maneuvering catheters (and associated guidewires) in and around the heart to deploy fluid bypass conduit device in accordance with embodiments of the present disclosure. For instance, access may be from above via either the subclavian or jugular veins into the superior vena cava 19, right atrium 5, and from there into the coronary sinus 16. Alternatively, the access path may start in the femoral vein and through the inferior vena cava 29 into the heart. Other access routes may also be used, some of which advantageously utilize a percutaneous incision through which the catheter 40 are inserted into the vasculature, normally through a sealed introducer, and from there the physician can control and navigate the distal end(s) of the devices from outside the body. The delivery catheter 40 can be advanced into the coronary sinus 16 through the coronary sinus ostium 66.

At block 904, the process 900 involves advancing the delivery catheter 40 through a wall 67 separating the coronary sinus 16 from the left atrium 2. The delivery catheter 40 may function to form and prepare the opening in the wall 67 of the left atrium, wherein a separate placement or delivery catheter is used for delivery of the fluid bypass conduit device. Alternatively, the deployment catheter 40 may be used as the both the puncture preparation and fluid bypass conduit device placement catheter.

Since the coronary sinus is largely contiguous around the left atrium, there are a variety of possible acceptable placements for the opening 65 in the wall 67. The site selected for the opening 65 may be made in an area where the tissue of the particular patient is less thick or less dense, as determined beforehand by non-invasive diagnostic means, such as a CT scan or radiographic technique, such as fluoroscopy or intravascular coronary echo (IVUS).

At block 906, the process 900 involves anchoring a first end of the fluid bypass conduit device transported in the catheter 40 in a target pulmonary vein 26 and/or associated ostium 25. The process 900 may involve deploying a distal end of the bypass fluid conduit device from the delivery catheter 40 for anchoring thereof. The conduit device 80 can comprise a generally tubular body or sleeve defining a lumen. The distal end of the conduit device 80 may serve as a fluid inlet. The distal end of the conduit device 80 may be associated with one or more anchoring features 81, which may be used to anchor the conduit device 80 to the pulmonary vein 26. The anchor feature(s) 81 may comprise, for example, one or more barb- or corkscrew-type tissue anchors and/or a stent form for anchoring to and/or in the pulmonary vein 26. Anchoring the distal end of the bypass fluid conduit 80 to the pulmonary vein 26 may involve embedding one or more barb tissue anchors associated with the distal end of the bypass fluid conduit 80 into biological tissue associated with the pulmonary vein 26. In some implementations, the process involves anchoring the distal end of the bypass fluid conduit 80 to another pulmonary vein using an anchor coupled to the anchor feature(s) 81 by an arm or clip member.

The bypass fluid conduit device 80 may be implanted at or in the pulmonary vein 26, 25 in such a way as to effectively fluid-seal the target pulmonary vein. Alternatively, the distal end of the conduit device 80 may be implanted or anchored at the pulmonary vein or pulmonary vein ostium in such a way as to include gaps or spaces around a periphery of the conduit device 80 through which blood may flow. Such gaps or spaces may be intentionally and/or deliberately allowed or implemented, or may result naturally from imperfect sealing or anchoring of the conduit device 80. Although the process 900 is described as involving first implanting the conduit device 80 in the pulmonary vein and secondly implanting the proximal end of the device 80 in the wall 67 between the left atrium 2 and the coronary sinus 16. in some implementations, the fluid bypass conduit device 80 may first be anchored to the wall 67, after which one or more of the pulmonary veins may be identified as providing a desired or ideal output or reduction in pressure, and such identified vein(s) may be coupled to the conduit device 80.

In some embodiments, the target pulmonary vein 26 may be selected to optimize an amount of blood flow shunted from the left side of the heart to the right. For example, the process 900 may involve selecting a desired one or number of pulmonary veins designed to provide the desired portion of the inlet blood flow from the lungs through the bypass conduit device 90.

At block 908, the process 900 involves withdrawing the delivery catheter 40 back to and/or through the wall 67 separating the coronary sinus 16 and left atrium 2, thereby deploying a medial channel portion of the fluid bypass conduit 80 and exposing the same in the left atrium 2. The bypass conduit device 80 may advantageously be at least partially self-expanding, and may include a jacket or cover, which may comprise thin PTEF material or similar, or biological tissue. The medial portion of the conduit device 80 can comprise an at least partially rigid frame, which may comprise an expandable laser-cut metal frame and/or one or more annular hoops covered by a sleeve or covering. The medial portion of the conduit device 80 may advantageously be at least partially flexible and may be pre-formed into a desired (e.g., at least partially curved) shape. The conduit device 80 can be advanced from the delivery catheter by pushing the conduit device 80 out of the delivery catheter 80 and/or retracting the delivery catheter 40 relative to the conduit device 80. In some implementations, a pusher device extending axially through at least a portion of the delivery catheter 40 may be used to assist in deploying the conduit device 80 from the catheter.

At block 910, the process 900 involves anchoring a proximal end of the fluid bypass conduit device 80 to the wall 67 between the atrium 2 and coronary sinus 16, such that the internal fluid channel of the conduit 80 provides a pathway from the pulmonary vein 26 through the wall 67 and into the right atrium 5. The anchor feature(s) 82 associated with the proximal end of the conduit device 80 may be any type of anchor features, including expanding coils or arms, or barb-type anchors configured to embed in the tissue of the wall 67. Anchoring the proximal end of the bypass fluid conduit 80 to the wall 67 separating the coronary sinus from the left atrium may comprise expanding a wire coil anchor associated with the proximal end of the bypass fluid conduit 80, the wire coil having a diameter that is greater than a diameter of the opening 65 in the wall 67 separating the coronary sinus 16 from the left atrium 2.

At block 912, the process 900 involves withdrawing the delivery catheter 40 from the heart of the patient, thereby leaving the fluid bypass implant device 80 implanted as shown in image 911. Due to the generally higher-pressure state in the left side of the heart compared to the right side of the heart, fluid back flow from the right atrium 5 to the left side of the heart may generally not occur in the steady-state implanted condition. With the delivery catheter withdrawn, the fluid bypass conduit device 80 can advantageously provide shunting from the left side of the heart to the right side of the heart, as described above. For example, the process 900 may further involve channeling blood from the pulmonary vein 26 to the coronary sinus 16 through the bypass fluid conduit 80.

As described in detail above, fluid bypass conduit devices in accordance with embodiments of the present disclosure may provide fluid coupling through the interatrial septum, which may provide a convenient location for conduit anchoring in view of the adjacency of the atria and the familiarity of transseptal access processes. However, there is generally a possibility of emboli travelling from the right side of the heart to the left, which presents a stroke risk. Such events generally only happen if the right atrium pressures go above left atrium pressures, such as during discrete events like coughing, sneezing, Valsalva maneuver, or bowel movements. The anatomical position of the septum would naturally allow emboli to travel between the right atrium and the pulmonary vein(s) was if the pressure gradient flips. This can be mitigated by a valve or filter element in the conduit device, but there may still be a risk that emboli will cross over.

Fluid coupling through the coronary sinus can offer certain benefits. For example, the coronary sinus can be much less likely to have emboli present for various reasons. First, the blood draining from the coronary vasculature into the right atrium has generally just passed through capillaries, so it is essentially filtered blood. Second, the ostium of the coronary sinus in the right atrium is often partially covered by a pseudo-valve called the Thebesian Valve. The Thebesian Valve is not always present, but some studies show it is present in >60% of hearts and can act as a natural filter to the coronary sinus to prevent emboli from entering in the event of a spike in right atrium pressure. Third, the pressure gradient between the coronary sinus and the right atrium into which it drains is generally very low, meaning that emboli in the right atrium is likely to remain there. Fourth, in the event that emboli do enter the coronary sinus, there is generally a much greater gradient between the right atrium and the coronary vasculature than between the right atrium and the left atrium. Most likely emboli would travel further down the coronary vasculature until right atrium pressure returned to normal and then the emboli would return directly to the right atrium.

Some additional advantages to bypassing blood through the coronary sinus is that this anatomy is less mobile and/or more stable than the septum. In addition, forming an opening in the wall between the coronary sinus and the left atrium rather than the interatrial septum preserves the septum for later transseptal access for alternate therapies. The preservation of transseptal access can represent a significant advantage because heart failure patients often have a number of other comorbidities, such as atrial fibrillation and mitral regurgitation, and several of the therapies for treating these conditions require a transseptal approach. Furthermore, by diverting left atrial blood into the coronary sinus, sinus pressures may increase by a small amount, thereby causing blood in the coronary vasculature to travel more slowly through the heart and increasing perfusion and oxygen transfer, which may improve cardiac efficiency and/or help dying heart muscle to recover.

Valve Spacer Integrated with Fluid Bypass Conduit Device

Figure 11:
FIG. 11 illustrates a heart having an integrated fluid bypass conduit and valve spacer device implanted therein in accordance with one or more embodiments.

Various embodiments described above provide means for shunting blood flow from one or more pulmonary veins to the right side of the heart. While some embodiments involve shunting blood flow from the pulmonary vein(s) to the right atrium, inventive solutions of the present disclosure also provide for shunting blood flow from one or more pulmonary veins to the right ventricle through the ventricular septum. Such shunting may be achieved using a fluid bypass conduit device 90 as shown in FIG. 11, which is configured to provide both blood flow shunting and mitral valve leaflet spacer functionality. In some embodiments, a valve leaflet spacer portion 99 of the conduit device, as shown in FIG. 11, is associated with the conduit device 90, and may be associated with certain reinforcement structure(s) (e.g., frame wire(s)) of the conduit device 90.

FIG. 11 illustrates a heart 1 having a fluid bypass conduit device 90 implanted therein. The fluid bypass conduit device 90 is configured to, when implanted in or adjacent to a pulmonary vein 26 and/or associated ostium 25 as shown, shunt blood flow from the pulmonary vein 26 to the right ventricle 4 to thereby reduce left atrial pressure. The distal end 94 of the fluid bypass conduit devices 90 may be anchored in any suitable or desirable way to the pulmonary vein 26 and/or pulmonary vein ostium 25, wherein a proximal end 92 of the conduit device 90 is anchored to and/or through the ventricular septum wall 17 to provide fluid access from the pulmonary vein 26 and/or left atrium 2 into the right side of the heart.

Access between the pulmonary vein 26 and the ventricular septum 17 may be achieved through the mitral valve 6, as shown. With a medial portion 99 of the conduit device 90 disposed and maintained in an intra-valvular position between the mitral valve leaflets 52, 54, the medial portion 99 may advantageously serve as a valve leaflet spacer to reduce mitral regurgitation. For example, the medial portion 99 of the conduit device 90 may at least partially fill a gap between the mitral leaflets 52, 54 that can give rise to mitral regurgitation. That is, in some patients, the mitral valve 6 represents a regurgitant orifice that negatively impacts cardiac efficiency and/or results in one or more other medical complications.

In some embodiments, at least the medial portion 99 of the conduit device is expandable to occupy a desired volume or space between the leaflets 52, 54. For example, the medial portion 99 may be pre-shaped to a desired spacer form/shape. In some implementations, the presence and form of the medial portion 99 of the conduit device 90 within the mitral valve 6 does not substantially alter the valve anatomy but advantageously provides a sealing surface for the leaflets, such that the medial portion 99 provides a new surface for coaptation for the native leaflets. The medial portion 99 of the conduit device 90 may have any suitable or desirable form and/or dimensions. In some embodiments, the medial portion 99 of the conduit device 90 has a maximum diameter of between 10-20 mm, such as 12, 15, or 18 mm.

With further reference to FIG. 11, the fluid bypass conduit device 90 may be configured and/or shaped such that blood flow from the pulmonary vein 26 is channeled at least partially within a lumen or channel of the implant device 90 into the right ventricle 4, thereby at least partially bypassing the left atrium 2 and/or ventricle 3. Attachment to the ventricular septum wall 17 may be made in such a way as to allow for blood flow through the septum 17 via the internal channel of the bypass conduit device 90. For example, a hole or opening may be formed in the septum 17 such that the implant bypass channel passes through the septal wall 17.

The ends of the implant device 90 may be sutured or anchored to their respective target tissue, such as a pulmonary vein and/or septal wall, in any suitable or desirable way. In some embodiments, the implant device 90 comprises a tubular, or partially-tubular, portion having one or more anchors associated with respective ends thereof. The tubular section, which may be considered to include the medial valve leaflet spacer portion 99, may advantageously comprise a self-expanding tubular structure. Furthermore, the fluid bypass conduit 90 may comprise a fluid-tight covering around at least a portion of the tubular frame component. In some embodiments, the tubular portion does not include an internal frame. The frame can be formed at least in part of one or more reinforcement structures configured to reinforce the conduit form of the fluid bypass conduit implant device 90 and/or valve leaflet spacer portion 99 thereof. The one or more reinforcement structures can be part of the covering that covers at least a portion of the medial portion 99 of the conduit form 90.

The anchor feature(s) 91, 93 associated with the respective ends of the fluid bypass conduit device 90 may be any type of tissue anchor or engagement feature(s). For example, in some embodiments, the anchor features 91, 93 comprise friction-fit, tissue-engagement anchors, such as one or more self-expanding stent features. The anchor features 91, 93 may additionally or alternatively comprise one or more wire and/or coil forms having a width or diameter dimension that serves to retain the respective end of the conduit device 90 in a desired position. Although a variety of features shown in FIG. 11, it should be understood that any of such features can be implemented independently of any of the other features shown and described.

FIG. 12 is a flow diagram illustrating a process 1000 for treating high left atrial pressure and mitral regurgitation in accordance with one or more embodiments of the present disclosure. At block 1002, the process 1000 involves advancing a delivery catheter to the right ventricle of a heart through a transapical access path. Although a transapical access path is described in FIG. 12, it should be understood that any access path may be utilized to access the right ventricle, including certain percutaneous procedures.

At block 1004, the process 1000 involves advancing the delivery catheter through the ventricular septum to access the left ventricle. At block 1006, the process 1000 involves advancing the delivery catheter through the mitral valve and into the left atrium from the left ventricle. At block 1008, the process 1000 involves advancing the delivery catheter adjacent to a target pulmonary vein, in a similar fashion as described herein in connection with other embodiments.

At block 1010, the process 1000 involves anchoring a first end (e.g., distal end) of a fluid bypass conduit device maintained at least partially within the delivery catheter to the target pulmonary vein and/or pulmonary vein ostium associated therewith. At block 1012, the process 1000 involves withdrawing the delivery catheter back to and/or through the mitral valve and ventricular septum. At block 1014, the process 1000 involves anchoring a second end (e.g., proximal end) of the fluid bypass conduit device to the ventricular septum. For example, the proximal end of the fluid bypass implant device may be anchored to the ventricular septum at, or adjacent to, the right ventricular side of the septum. After both ends of the fluid bypass conduit device have been successfully anchored, the delivery catheter may be withdrawn from the heart.

Additional Embodiments

Depending on the embodiment, certain acts, events, or functions of any of the processes described herein can be performed in a different sequence, may be added, merged, or left out altogether. Thus, in certain embodiments, not all described acts or events are necessary for the practice of the processes.

Certain standard anatomical terms of location are used herein with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. Spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present. As used herein, the term "and/or" used between the last two of a list of elements means any one or more of the listed elements. For example, the phrase "A, B, and/or C" means "A," "B," "C," "A and B," "A and C," "B and C," or "A, B, and C."

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

With respect to the various methods and processes disclosed herein, although certain orders of operations or steps are illustrated and/or described, it should be understood that the various steps and operations shown and described may be performed in any suitable or desirable temporal order. Furthermore, any of the illustrated and/or described operations or steps may be omitted from any given method or process, and the illustrated/described methods and processes may include additional operations or steps not explicitly illustrated or described.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

What is claimed is:

1. A method of reducing left atrial pressure for treating heart failure and improving heart function, the method comprising:

advancing a delivery catheter to a right atrium of a heart of a patient via a transcatheter access path;

advancing the delivery catheter into a coronary sinus;

advancing the delivery catheter through a wall separating the coronary sinus from a left atrium of the heart;

deploying a distal end of a bypass fluid conduit from the delivery catheter;

anchoring the distal end of the bypass fluid conduit to a pulmonary vein, the distal end of the bypass fluid conduit comprising a distal axial inlet that is co-axial with an axis of the bypass fluid conduit;

withdrawing the delivery catheter through the wall separating the coronary sinus from the left atrium, thereby exposing at least a portion of a medial segment of the bypass fluid conduit in the left atrium;

anchoring a proximal end of the bypass fluid conduit to the wall separating the coronary sinus from the left atrium to thereby form a direct shunt flow channel from the pulmonary vein into the coronary sinus; and withdrawing the delivery catheter from the heart;

wherein the distal axial inlet of the bypass fluid conduit seals the pulmonary vein without gaps between an outer diameter of the bypass fluid conduit and an inner wall of the pulmonary vein in a manner as to force blood flow of the pulmonary vein into the medial segment of the bypass fluid conduit via the distal axial inlet for shunting to the right atrium via the coronary sinus, thereby reducing blood pressure in the left atrium for treating heart failure.

2. The method of claim 1, wherein said anchoring the distal end of the bypass fluid conduit to the pulmonary vein comprises embedding one or more barb tissue anchors associated with the distal end of the bypass fluid conduit into biological tissue associated with the pulmonary vein.

3. The method of claim 1, wherein the bypass fluid conduit comprises:

a self-expanding memory metal frame dimensioned to extend from the pulmonary vein to the wall separating the coronary sinus from the left atrium; and an at least partially fluid-tight covering disposed over at least a portion of the self-expanding memory metal frame.

4. The method of claim 1, wherein the proximal end of the bypass fluid conduit comprises a wire coil anchor having a diameter that is greater than a diameter of the bypass fluid conduit.

5. The method of claim 1, further comprising anchoring the distal end of the bypass fluid conduit to another pulmonary vein using an anchor coupled to the distal end of the bypass fluid conduit by an arm member.

6. A method of managing left atrial pressure, the method comprising:

advancing a delivery catheter to a right atrium of a heart of a patient via a transcatheter access path;

advancing the delivery catheter into a coronary sinus;

forming an opening in a wall of the coronary sinus;

passing the delivery catheter through the wall of the coronary sinus and into a left atrium of the heart of a patient;

deploying a distal end of a bypass fluid conduit from the delivery catheter, wherein the bypass fluid conduit is an elongate tube formed with a lumen having a substantially constant diameter;

securing the distal end of the bypass fluid conduit to a first left pulmonary vein, such that blood flow exiting the first left pulmonary vein is forced into a tubular distal axial inlet of the bypass fluid conduit that is aligned with an axis of the bypass fluid conduit;

anchoring a proximal end of the bypass fluid conduit to a tissue wall associated with the coronary sinus to thereby form a direct shunt flow channel from the first left pulmonary vein into the coronary sinus to divert 25% of total oxygenated blood flow from lungs of the patient; and withdrawing the delivery catheter from the heart;

wherein the 25% of the total oxygenated blood is diverted such that no blood from the first left pulmonary vein enters the left atrium, thereby reducing left atrial pressure and alleviating heart failure symptoms and improving heart function.

7. The method of claim 6, wherein sealing-off the opening of the first left pulmonary vein includes expanding a self-expanding stent structure associated with the distal end of the bypass fluid conduit within the first left pulmonary vein.

8. The method of claim 6, wherein the proximal end of the bypass fluid conduit comprises a wireform coil that is expandable.

9. The method of claim 6, wherein the bypass fluid conduit comprises a metal frame having a biocompatible, fluid-tight covering.

10. The method of claim 6, wherein sealing-off the opening of the first left pulmonary vein involves embedding barbs associated with the distal end of the bypass fluid conduit in an inner wall of the first left pulmonary vein, the barbs extending distally from the distal end of the bypass fluid conduit and curving around to project in a proximal direction.

11. The method of claim 6, wherein the tissue wall is a coronary sinus septum.

12. The method of claim 6, wherein the tissue wall separates the left atrium from the coronary sinus.

13. The method of claim 6, further comprising:

expanding a first stent in the first left pulmonary vein, the first stent being associated with the distal end of the bypass fluid conduit; and expanding a second stent in a second left pulmonary vein, the second stent being coupled to the first stent by a bridge member.

14. The method of claim 6, further comprising anchoring the distal end of the bypass fluid conduit to a second left pulmonary vein using an anchor coupled to the distal end of the bypass fluid conduit by an arm member.

15. The method of claim 6, wherein the bypass fluid conduit has associated therewith an accordion feature configured to axially contract to cause axial contraction of the bypass fluid conduit.

16. The method of claim 15, wherein the accordion feature comprises a plurality of pleated layers of a covering of the bypass fluid conduit.

17. A method of managing left atrial pressure, the method comprising:

advancing a delivery catheter to a right atrium of a heart of a patient via a transcatheter access path;

advancing the delivery catheter into a coronary sinus;

advancing the delivery catheter through a tissue wall that separates a left atrium of the heart from the coronary sinus;

deploying a distal end of a fluid-tight shunt tube from the delivery catheter, the fluid-tight shunt tube comprising a self-expanding frame and a fabric covering;

anchoring the distal end of the fluid-tight shunt tube to a pulmonary vein, the distal end of the fluid-tight shunt tube comprising a distal axial inlet aligned with an axis of the fluid-tight shunt tube;

withdrawing the delivery catheter through the tissue wall, thereby exposing at least a portion of a medial segment of the fluid-tight shunt tube in the left atrium;

anchoring a plurality of anchor arms emanating from a proximal end of the fluid-tight shunt tube within the coronary sinus, thereby providing fluid access from the pulmonary vein into the coronary sinus from the fluid-tight shunt tube; and withdrawing the delivery catheter from the heart;

wherein the distal axial inlet of the fluid-tight shunt tube is sized such that an outer diameter thereof contacts an inner wall of the pulmonary vein around a circumference of the fluid-tight shunt tube to seal the pulmonary vein in a manner as to force blood flow of the pulmonary vein into the medial segment of the fluid-tight shunt tube via the distal axial inlet for shunting to a right side of the heart via the coronary sinus to reduce left atrial pressure.

18. The method of claim 17, wherein withdrawing the delivery catheter through the tissue wall involves withdrawing the delivery catheter through the coronary sinus.

\* \* \* \* \*